(12) United States Patent
Amine et al.

(10) Patent No.: US 11,108,086 B2
(45) Date of Patent: Aug. 31, 2021

(54) ELECTROLYTE FOR HIGH VOLTAGE LITHIUM-ION BATTERIES

(71) Applicant: UChicago Argonne, LLC, Chicago, IL (US)

(72) Inventors: Khalil Amine, Oakbrook, IL (US); Chi Cheung Su, Westmont, IL (US); Meinan He, Willowbrook, IL (US); Tianyuan Ma, Darien, IL (US)

(73) Assignee: UChicago Argonne, LLC, Chicago, IL (US)

( * ) Notice: Subject to any disclaimer, the term of this patent is extended or adjusted under 35 U.S.C. 154(b) by 380 days.

(21) Appl. No.: 15/885,148

(22) Filed: Jan. 31, 2018

(65) Prior Publication Data
US 2019/0233388 A1  Aug. 1, 2019

(51) Int. Cl.
H01M 10/0567 (2010.01)
C07D 327/10 (2006.01)
H01M 10/0525 (2010.01)
H01M 10/054 (2010.01)
H01M 10/0568 (2010.01)
H01M 10/052 (2010.01)
H01M 10/0569 (2010.01)
H01M 4/583 (2010.01)
H01M 4/133 (2010.01)

(52) U.S. Cl.
CPC ...... *H01M 10/0567* (2013.01); *C07D 327/10* (2013.01); *H01M 4/133* (2013.01); *H01M 4/583* (2013.01); *H01M 10/052* (2013.01); *H01M 10/054* (2013.01); *H01M 10/0525* (2013.01); *H01M 10/0568* (2013.01); *H01M 10/0569* (2013.01); *H01M 2300/0034* (2013.01); *H01M 2300/0037* (2013.01)

(58) Field of Classification Search
CPC ......... H01M 10/0567; H01M 10/0568; H01M 10/0569; H01M 10/0525; H01M 10/054; H01M 10/052; H01M 2300/0037; H01M 2300/0034; H01M 4/583; H01M 4/133; C07D 327/10
See application file for complete search history.

(56) References Cited

U.S. PATENT DOCUMENTS

2003/0113636 A1   6/2003  Sano et al.
2016/0072150 A1*  3/2016  Kim ............... H01M 10/0567
                                                429/200
2017/0084951 A1   3/2017  Dubois et al.

FOREIGN PATENT DOCUMENTS

CN   102646847 A   8/2012
JP   10-189042 A   7/1998

* cited by examiner

*Primary Examiner* — Laura Weiner
(74) *Attorney, Agent, or Firm* — Foley & Lardner LLP

(57) ABSTRACT

An electrolyte, electrochemical device, battery, capacitor, and/or the like include a salt; and a fluorinated organosulfate compound represented by Formula I:

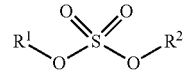

Formula I wherein, $R^1$ is H, $OR^3$, alkyl, alkenyl, alkynyl, aralkyl, or silyl; $R^2$ is H, $OR^3$, alkyl, alkenyl, alkynyl, aralkyl, or silyl; and $R^3$ is H, alkyl, alkenyl, alkynyl, aryl, heterocyclyl, heteroaryl, or siloxy; or where $R^1$ and $R^2$ join together to form a cyclic compound incorporating the —O—S(O)$_2$—O— group; wherein at least one $R^1$ and $R^2$ is fluorinated.

11 Claims, 10 Drawing Sheets

ELECTROLYTE FOR HIGH VOLTAGE LITHIUM-ION BATTERIES

GOVERNMENT RIGHTS

The United States Government has rights in this invention pursuant to Contract No. DE-AC02-06CH11357 between the U.S. Department of Energy and UChicago Argonne, LLC, representing Argonne National Laboratory.

FIELD

The present technology is generally related to lithium rechargeable batteries. More particularly the technology relates to the use of fluorinated organosulfate compounds in electrochemical cells and batteries.

BACKGROUND

Lithium-ion batteries (LIBs) are widely used as electrical power for consumer electronics and hybrid electric vehicles. To facilitate the extensive application of pure electric vehicles, LIBs with high energy density are essential. An effective way to enhance the energy density of lithium-ion batteries is to increase the operating voltage of the cells by increasing the working potentials of the positive electrode employed. However, cycling of the cell to high voltage suffers from low Coulombic efficiency and fast capacity fading due to the anodic instability of the conventional electrolytes at voltages higher than 4.5 V vs $Li^+/Li$.

For example, the Ni-rich cathode NMC532, is capable of delivering higher capacity when operated at elevated potentials (>4.4 V). However, the battery performance fades rapidly at such potentials due to the parasitic reaction of the state-of-the-art electrolytes on the cathode surface, causing transition metal ion dissolution into the electrolyte solution.

State-of-the-art lithium-ion battery electrolytes include a 1.0-1.5 M lithium hexafluorophosphate ($LiPF_6$) dissolved in a mixture of ethylene carbonate (EC) with dimethyl carbonate (DMC), diethyl carbonate (DEC), and/or ethyl methyl carbonate (EMC). Owing to its outstanding solid-electrolyte interface (SEI) forming properties, cyclic carbonate EC is an essential electrolyte solvent in conventional electrolyte system. However, the high melting point (36° C.) of EC limits the low temperature application of lithium-ion batteries utilizing conventional electrolyte. Other potential solvents such as propylene carbonate (PC), which is a cyclic carbonate with low melting point (−49° C.), fail to provide satisfactory passivation of graphite due to its co-intercalation with lithium cation into the crystal structure of graphite. More importantly, the low anodic stability of EC renders severe electrolyte decomposition in high-voltage lithium-ion cells.

SUMMARY

In one aspect, an electrolyte is provided, the electrolyte including a salt; and a fluorinated organosulfate compound represented by Formula I:

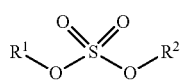

Formula I

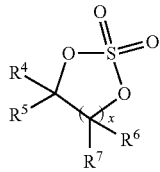

Formula II

In Formula I and II:
$R^1$ is alkyl, $R^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;

$R^2$ is alkyl, $R^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;

$R^3$ is H, alkyl, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;

x is 1 or 2;

$R^4$ is H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)$OR^8$, —OC(O)$R^8$;

$R^5$ is H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)$OR^8$, —OC(O)$R^8$;

each $R^6$ is individually H, F, $OR^8$, alkyl, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, —C(O)$OR^8$, —OC(O)$R^8$;

each $R^7$ is individually H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)$OR^8$, —OC(O)$R^8$;

or wherein $R^4$ and $R^5$ or $R^6$ and $R^7$ join together to form an =O group;

each $R^8$ is individually H, alkyl, alkenyl, aralkyl, polyalkylene glycol, or silyl; and at least one of $R^1$ and $R^2$ in Formula I is a fluorinated group, and/or at least one of $R^4$, $R^5$, $R^6$, or $R^7$ in Formula II is fluorine or is a fluorinated group.

In some embodiments, at least one of $R^1$ and $R^2$ is —$CFH_2$; —$CF_2H$; —$CF_3$; —$CF_2CF_3$; —$CF_2CHF_2$; —$CF_2CH_3$; —$CF_2CH_2F$; —$CHFCF_3$; —$CHFCHF_2$; —$CHFCH_3$; —$CHFCH_2F$; —$CH_2CF_3$; —$CH_2CHF_2$; —$CH_2CH_2F$; —$CF(CF_3)_2$; —$CH(CF_3)_2$; —$CF_2CF_2CF_3$; —$CF_2CF_2CHF_2$; —$CF_2CF_2CH_3$; —$CF_2CF_2CH_2F$; —$CH_2CF_2CF_3$; —$CH_2CF_2CHF_2$; —$CH_2CF_2CH_3$; —$CH_2CF_2CH_2F$; —$CHFCF_2CF_3$; —$CHFCF_2CHF_2$; —$CHFCF_2CH_3$; —$CHFCF_2CH_2F$; —$CF_2CH_2CF_3$; —$CF_2CH_2CHF_2$; —$CF_2CH_2CH_3$; —$CF_2CH_2CH_2F$; —$CF_2CHFCF_3$; —$CF_2CHFCHF_2$; —$CF_2CHFCH_3$; —$CF_2CHFCH_2F$; —$CHFCHFCF_3$; —$CHFCHFCHF_2$; —$CHFCHFCH_3$; —$CHFCHFCH_2F$; $CH_2CH_2CF_3$; —$CH_2CH_2CHF_2$; —$CH_2CH_2CH_2F$; —$CF_2CF_2CF_2CF_3$; —$CF_2CF_2CF_2CH_3$; —$CF_2CF_2CF_2CHF_2$; —$CF_2CF_2CF_2CH_2F$; —$CH_2CF_2CF_2CF_3$; —$CH_2CF_2CF_2CH_3$; —$CH_2CF_2CF_2CHF_2$; —$CH_2CF_2CF_2CH_2F$; —$CHFCF_2CF_2CF_3$; —$CHFCF_2CF_2CH_3$; —$CHFCF_2CF_2CHF_2$; —$CHFCF_2CF_2CH_2F$; —$CF_2CH_2CF_2CF_3$;

—CF$_2$CH$_2$CF$_2$CH$_3$;  —CF$_2$CH$_2$CF$_2$CHF$_2$;
—CF$_2$CH$_2$CF$_2$CH$_2$F;  —CF$_2$CHFCF$_2$CF$_3$;
—CF$_2$CHFCF$_2$CH$_3$;  —CF$_2$CHFCF$_2$CHF$_2$;
—CF$_2$CHFCF$_2$CH$_2$F;  —CHFCHFCF$_2$CF$_3$;
—CHFCHFCF$_2$CH$_3$;  —CHFCHFCF$_2$CHF$_2$;
—CHFCHFCF$_2$CH$_2$F;  —CH$_2$CH$_2$CF$_2$CF$_3$;
—CH$_2$CH$_2$CF$_2$CH$_3$;  —CH$_2$CH$_2$CF$_2$CHF$_2$;
—CH$_2$CH$_2$CF$_2$CH$_2$F;  —CF$_2$CF$_2$CF$_2$CF$_2$CF$_3$;
—CH$_2$CF$_2$CF$_2$CF$_2$CF$_3$;  —CF$_2$CF$_2$CF$_2$CF$_2$CHF$_2$;
—CH$_2$CF$_2$CF$_2$CF$_2$CHF$_2$; —CF$_2$OCFH$_2$; —CF$_2$OCF$_2$H;
—CF$_2$OCF$_3$;  —CF$_2$OCF$_2$CF$_3$;  —CF$_2$OCF$_2$CHF$_2$;
—CF$_2$OCF$_2$CH$_3$; —CF$_2$OCF$_2$CH$_2$F; —CF$_2$OCHFCF$_3$;
—CF$_2$OCHFCHF$_2$; —CF$_2$OCHFCH$_3$; —CF$_2$OCHFCH$_2$F;
—CF$_2$OCH$_2$CF$_3$; —CF$_2$OCH$_2$CHF$_2$; —CF$_2$OCH$_2$CH$_2$F;
—CH$_2$OCFH$_2$;  —CH$_2$OCF$_2$H;  —CH$_2$OCF$_3$;
—CH$_2$OCF$_2$CF$_3$; —CH$_2$OCF$_2$CHF$_2$; —CH$_2$OCF$_2$CH$_3$;
—CH$_2$OCF$_2$CH$_2$F; —CH$_2$OCHFCF$_3$; —CH$_2$OCRFCHF$_2$;
—CH$_2$OCHFCH$_3$; —CH$_2$OCHFCH$_2$F; —CH$_2$OCH$_2$CF$_3$;
—CH$_2$OCH$_2$CHF$_2$; —CH$_2$OCH$_2$CH$_2$F; —CHFOCFH$_2$;
—CHFOCF$_2$H;  —CHFOCF$_3$;  —CHFOCF$_2$CF$_3$;
—CHFOCF$_2$CHF$_2$; —CHFOCF$_2$CH$_3$; —CHFOCF$_2$CH$_2$F;
—CHFOCHFCF$_3$; —CHFOCHFCHF$_2$; —CHFOCHFCH$_3$;
—CHFOCHFCH$_2$F;  —CHFOCH$_2$CF$_3$;
—CHFOCH$_2$CHF$_2$; or —CHFOCH$_2$CH$_2$F.

In any of the above embodiments, the electrolyte may also include a non-aqueous solvent. In some embodiments, the non-aqueous solvent may be a non-fluorinated, non-aqueous solvent. In some embodiments, the electrolyte may also include a lithium salt or a sodium salt.

In another aspect, an electrochemical device is provided, the device including a cathode; an anode; and an electrolyte; wherein the electrolyte is any of the above, or herein disclosed electrolytes.

DETAILED DESCRIPTION

Figure 1:
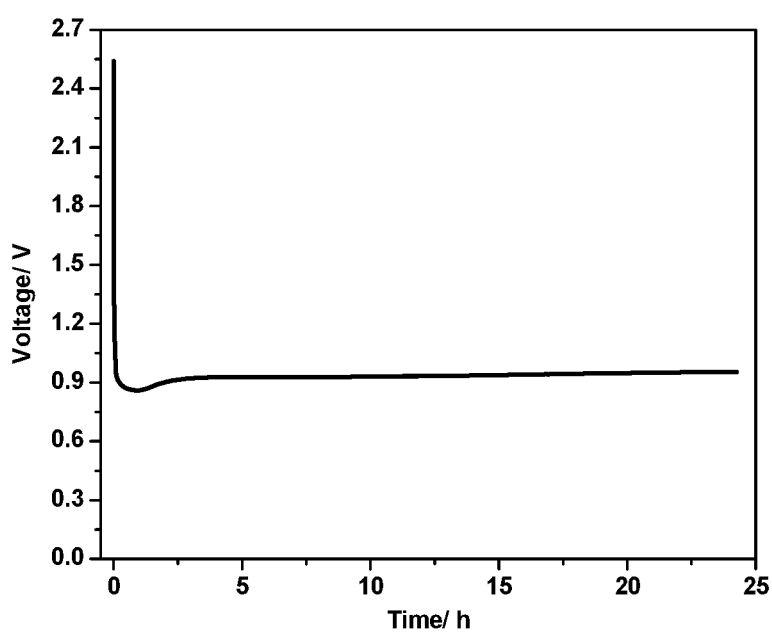
FIG. 1 is a graph illustrating the voltage profile of cells using 1.0M LiPF$_6$PC:EC at a weight ratio 4:1 using a cathode of graphite, an anode of lithium metal, according to Example 1.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Conventional electrolytes for Li-ion batteries typically include lithium hexafluorophosphate (LiPF$_6$) dissolved in a cyclic carbonate and linear carbonate. The cyclic carbonate, which is typically, ethylene carbonate (EC), for most of the conventional electrolyte, decomposes sacrificially on the graphite surface to form a solid electrolyte interface (SEI) that can kinetically prevent further reduction of electrolyte and facilitate the cycling of the battery. However, the relatively low oxidation potential of EC prevents its application in high voltage cathode and the SEI formed by EC decomposition is also far from perfect. Thus, it is important to develop new SEI enabler which has better high voltage stability and forms more robust SEI on the anode surface.

As illustrated in the examples herein, 1,3,2-dioxathiolane-2,2-dioxide (ethylene sulfate, DTD) shows good cycling stability, however, the melting point is substantial (96° C.) and does not lend itself to use in low temperature applications. Addition of the methyl group to form 4-methyl-1,3,2-dioxathiolane 2,2-dioxide (propylene sulfate, MDTD) significantly reduces the melting point to 46° C. However, MDTD decomposes readily upon storage. The freshly distilled pure colorless liquid of MDTD turns dark brown within a week even when it is stored inside argon glovebox. Commercially available MDTD all appears to be dark thick liquid because of the decomposition pathways illustrated in Scheme 2 (vide infra). Although the degradation of DTD is significantly slower due to its solid nature, DTD also turns dark in glovebox upon prolonged storage (>3 months). Thus, the development of cyclic sulfate with long storage time and higher oxidation stability is vital to its application in high voltage Li-ion batteries.

The present inventors have now found that the fluorinated organosulfate compounds described herein provide excellent solid electrolyte interface (SEI) forming abilities and are stable when subject to high oxidation potentials. Such compounds provide for enhanced overall stability of the electrolytes incorporating the compounds, which in turn provide improved electrochemical cell and battery performance, because the composition inhibit oxidative decomposition of the batteries. The electrolyte may be used in lithium ion batteries as well as sodium-ion batteries.

In one aspect, an electrolyte is provided that includes a salt and a fluorinated organosulfate compound represented by Formula I:

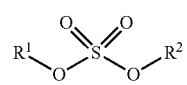

Formula I

In Formula I, R$^1$ may be alkyl, R$^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, or silyl, R$^2$ may be alkyl, R$^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, or silyl, and R$^3$ is H, alkyl, cycloalkyl, cycloalkylalkyl, alkenyl, alkynyl, aryl, aralkyl, heterocyclyl, heterocyclylalkyl, heteroaryl, heteroarylalkyl, or siloxy, or where R$^1$ and R$^2$ may join together to form a cyclic compound incorporating the O—S(O)$_2$—O— group, with the proviso that at least one $R^1$ and $R^2$ is fluorinated. In any of the above embodiments, $R^1$ may be $C_1$-$C_{12}$ alkyl, $C_1$-$C_{12}$ alkenyl, $C_1$-$C_{12}$ alkynyl, $C_7$-$C_{17}$ aralkyl, $C_7$-$C_{17}$ heteroarylalkyl, $C_7$-$C_{17}$ heterocyclylalkyl, $C_7$-$C_{17}$ cycloalkylalkyl, or silyl, and $R^2$ may be $C_1$-$C_{12}$ alkyl, $C_1$-$C_{12}$ alkenyl, $C_1$-$C_{12}$ alkynyl, $C_7$-$C_{17}$ aralkyl, $C_7$-$C_{17}$ heteroarylalkyl, $C_7$-$C_{17}$ heterocyclylalkyl, $C_7$-$C_{17}$ cycloalkylalkyl, or silyl.

In any of the above embodiments, one or both of $R^1$ and $R^2$ may be $OR^3$, wherein $R^3$ is H, alkyl, alkenyl, alkynyl, aryl, heteroaryl, heterocycyl, cycloalkyl, aralkyl, heteroarylalkyl, heterocyclylalkyl, or cycloalkylalkyl. In some embodiments, $R^3$ is H, $C_1$-$C_{12}$ alkyl, $C_1$-$C_{12}$ alkenyl, $C_1$-$C_{12}$ alkynyl, $C_7$-$C_{17}$ aralkyl, $C_7$-$C_{17}$ heteroarylalkyl, $C_7$-$C_{17}$ heterocyclylalkyl, or $C_7$-$C_{17}$ cycloalkylalkyl.

In any of the above embodiments, at least one of $R^1$ and $R^2$ may be —CFH$_2$; —CF$_2$H; —CF$_3$; —CF$_2$CF$_3$; —CF$_2$CHF$_2$; —CF$_2$CH$_3$; —CF$_2$CH$_2$F; —CHFCF$_3$; —CHFCHF$_2$; —CHFCH$_3$; —CHFCH$_2$F; —CH$_2$CF$_3$; —CH$_2$CHF$_2$; —CH$_2$CH$_2$F; —CF(CF$_3$)$_2$; —CH(CF$_3$)$_2$; —CF$_2$CF$_2$CF$_3$; —CF$_2$CF$_2$CHF$_2$; —CF$_2$CF$_2$CH$_3$; —CF$_2$CF$_2$CH$_2$F; —CH$_2$CF$_2$CF$_3$; —CH$_2$CF$_2$CHF$_2$; —CH$_2$CF$_2$CH$_3$; —CH$_2$CF$_2$CH$_2$F; —CHFCF$_2$CF$_3$; —CHFCF$_2$CHF$_2$; —CHFCF$_2$CH$_3$; —CHFCF$_2$CH$_2$F; —CF$_2$CH$_2$CF$_3$; —CF$_2$CH$_2$CHF$_2$; —CF$_2$CH$_2$CH$_3$; —CF$_2$CH$_2$CH$_2$F; —CF$_2$CHFCF$_3$; —CF$_2$CHFCHF$_2$; —CF$_2$CHFCH$_3$; —CF$_2$CHFCH$_2$F; —CHFCHFCF$_3$; —CHFCHFCHF$_2$; —CHFCHFCH$_3$; —CHFCHFCH$_2$F; CH$_2$CH$_2$CF$_3$; —CH$_2$CH$_2$CHF$_2$; —CH$_2$CH$_2$CH$_2$F; —CF$_2$CF$_2$CF$_2$CF$_3$; —CF$_2$CF$_2$CF$_2$CH$_3$; —CF$_2$CF$_2$CF$_2$CHF$_2$; —CF$_2$CF$_2$CF$_2$CH$_2$F; —CH$_2$CF$_2$CF$_2$CF$_3$; —CH$_2$CF$_2$CF$_2$CH$_3$; —CH$_2$CF$_2$CF$_2$CHF$_2$; —CH$_2$CF$_2$CF$_2$CH$_2$F; —CHFCF$_2$CF$_2$CF$_3$; —CHFCF$_2$CF$_2$CH$_3$; —CHFCF$_2$CF$_2$CHF$_2$; —CHFCF$_2$CF$_2$CH$_2$F; —CF$_2$CH$_2$CF$_2$CF$_3$; —CF$_2$CH$_2$CF$_2$CH$_3$; —CF$_2$CH$_2$CF$_2$CHF$_2$; —CF$_2$CH$_2$CF$_2$CH$_2$F; —CF$_2$CHFCF$_2$CF$_3$; —CF$_2$CHFCF$_2$CH$_3$; —CF$_2$CHFCF$_2$CHF$_2$; —CF$_2$CHFCF$_2$CH$_2$F; —CHFCHFCF$_2$CF$_3$; —CHFCHFCF$_2$CH$_3$; —CHFCHFCF$_2$CHF$_2$; —CHFCHFCF$_2$CH$_2$F; —CH$_2$CH$_2$CF$_2$CF$_3$; —CH$_2$CH$_2$CF$_2$CH$_3$; —CH$_2$CH$_2$CF$_2$CHF$_2$; —CH$_2$CH$_2$CF$_2$CH$_2$F; —CF$_2$CF$_2$CF$_2$CF$_2$CF$_3$; —CH$_2$CF$_2$CF$_2$CF$_2$CF$_3$; —CF$_2$CF$_2$CF$_2$CF$_2$CHF$_2$; —CH$_2$CF$_2$CF$_2$CF$_2$CHF$_2$; —CF$_2$OCFH$_2$; —CF$_2$OCF$_2$H; —CF$_2$OCF$_3$; —CF$_2$OCF$_2$CF$_3$; —CF$_2$OCF$_2$CHF$_2$; —CF$_2$OCF$_2$CH$_3$; —CF$_2$OCF$_2$CH$_2$F; —CF$_2$OCHFCF$_3$; —CF$_2$OCHFCHF$_2$; —CF$_2$OCHFCH$_3$; —CF$_2$OCHFCH$_2$F; —CF$_2$OCH$_2$CF$_3$; —CF$_2$OCH$_2$CHF$_2$; —CF$_2$OCH$_2$CH$_2$F; —CH$_2$OCFH$_2$; —CH$_2$OCF$_2$H; —CH$_3$,OCF$_3$; —CH$_2$OCF$_2$CF$_3$; —CH$_2$OCF$_2$CHF$_2$; —CH$_2$OCF$_2$CH$_3$; —CH$_2$OCF$_2$CH$_2$F; —CH$_2$OCHFCF$_3$; —CH$_2$OCHFCHF$_2$; —CH$_2$OCHFCH$_3$; —CH$_2$OCHFCH$_2$F; —CH$_2$OCH$_2$CF$_3$; —CH$_2$OCH$_2$CHF$_2$; —CH$_2$OCH$_2$CH$_2$F; —CHFOCFH$_2$; —CHFOCF$_2$H; —CHFOCF$_3$; —CHFOCF$_2$CF$_3$; —CHFOCF$_2$CHF$_2$; —CHFOCF$_2$CH$_3$; —CHFOCF$_2$CH$_2$F; —CHFOCHFCF$_3$; —CHFOCHFCHF$_2$; —CHFOCHFCH$_3$; —CHFOCHFCH$_2$F; —CHFOCH$_2$CF$_3$; —CHFOCH$_2$CHF$_2$; or —CHFOCH$_2$CH$_2$F. In some embodiments, $R^1$ and $R^2$ are individually —CFH$_2$; —CF$_2$H; —CF$_3$; —CF$_2$CF$_3$; —CF$_2$CHF$_2$; —CF$_2$CH$_3$; —CF$_2$CH$_2$F; —CHFCF$_3$; —CHFCHF$_2$; —CHFCH$_3$; —CHFCH$_2$F; —CH$_2$CF$_3$; —CH$_2$CHF$_2$; —CH$_2$CH$_2$F; —CF(CF$_3$)$_2$; —CH(CF$_3$)$_2$; —CF$_2$CF$_2$CF$_3$; —CF$_2$CF$_2$CHF$_2$; —CF$_2$CF$_2$CH$_3$; —CF$_2$CF$_2$CH$_2$F; —CH$_2$CF$_2$CF$_3$; —CH$_2$CF$_2$CHF$_2$; —CH$_2$CF$_2$CH$_3$; —CH$_2$CF$_2$CH$_2$F; —CHFCF$_2$CF$_3$; —CHFCF$_2$CHF$_2$; —CHFCF$_2$CH$_3$; —CHFCF$_2$CH$_2$F; or —CF$_2$CH$_2$CF$_3$. In some embodiments, $R^1$ and $R^2$ are —CH$_2$CF$_3$.

In the compound of Formula I, $R^1$ and $R^2$ may join together to form a cyclic compound of Formula II:

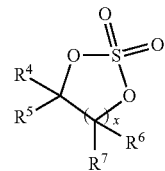

Formula II

In Formula II, x may be 1 or 2; $R^4$ may be H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, or —OC(O)R$^8$; $R^5$ may be H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, or —OC(O)R$^8$; each $R^6$ may be individually H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, or —OC(O)R$^8$; each $R^7$ may be individually H, F, $OR^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, or —OC(O)R$^8$; each $R^8$ may be H, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, or siloxy; or wherein $R^4$ and $R^5$ or $R^6$ and $R^7$ may join together to form an =O group; and at least one $R^4$, $R^5$, $R^6$, or $R^7$ is fluorine or is a fluorinated group. In some embodiments of Formula II $R^4$ may be H, F, $OR^8$, $C_1$-$C_{12}$ alkyl, $C_1$-$C_{12}$ alkenyl, $C_7$-$C_{16}$ aralkyl, silyl, an ether, —C(O)OR$^8$, or —OC(O)R$^8$; $R^5$ may be H, F, $OR^8$, $C_1$-$C_{12}$ alkyl, $C_1$-$C_{12}$ alkenyl, $C_7$-$C_{16}$ aralkyl, silyl, an ether, —C(O)OR$^8$, or —OC(O)R$^8$; each $R^6$ may be individually H, F, $OR^8$, $C_1$-$C_{12}$ alkyl, $C_1$-$C_{12}$ alkenyl, $C_7$-$C_{16}$ aralkyl, silyl, an ether, —C(O)OR$^8$, or —OC(O)R$^8$; each $R^7$ may be individually H, F, $OR^8$, alkyl, alkenyl, aralkyl, silyl, an ether, —C(O)OR$^8$, or —OC(O)R$^8$; each $R^8$ may be H, $C_1$-$C_{12}$ alkyl, $C_1$-$C_{12}$ alkenyl, $C_7$-$C_{16}$ aralkyl, or silyl; or wherein $R^4$ and $R^5$ or $R^6$ and $R^7$ may join together to form an =O group; and at least one $R^4$, $R^5$, $R^6$, or $R^7$ is fluorine or is a fluorinated group.

In the compound of Formula II, $R^4$, $R^5$, $R^6$, or $R^7$ may individually be, in some embodiments, methoxy, vinyl, propargyl, benzyl, heterocyclyloxy, alkenoxy, alkynoxy, aryloxy, heterocyclylalkoxy, oxo; carboxyl, an ester group, or an ether. In some embodiments of Formula II, $R^4$, $R^5$, $R^6$, or $R^7$ may individually be, —CH$_{3-x}$F$_x$, —(CH$_n$F$_x$)$_n$CH$_{3-x}$F$_x$, —(CH$_n$F$_x$)$_n$O(CH$_n$F$_x$)$_n$CH$_{3-x}$F$_x$, —CH$_2$CH$_2$O$_n$CH$_x$F$_y$, or —CF$_2$OC$_n$H$_x$F$_y$, where n is from 0 to 12; x is 1, 2, or 3; n' is 0, 1, or 2; and x' is 0, 1, or 2.

In any of the above embodiments, at least one of $R^4$, $R^5$, $R^6$, and $R^7$ may be —F; —CFH$_2$; —CF$_2$H; —CF$_3$; —CF$_2$CF$_3$; —CF$_2$CHF$_2$; —CF$_2$CH$_3$; —CF$_2$CH$_2$F; —CHFCF$_3$; —CHFCHF$_2$; —CHFCH$_3$; —CHFCH$_2$F; —CH$_2$CF$_3$; —CH$_2$CHF$_2$; —CH$_2$CH$_2$F; —CF(CF$_3$)$_2$; —CH(CF$_3$)$_2$; —CF$_2$CF$_2$CF$_3$; —CF$_2$CF$_2$CHF$_2$; —CF$_2$CF$_2$CH$_3$; —CF$_2$CF$_2$CH$_2$F; —CH$_2$CF$_2$CF$_3$; —CH$_2$CF$_2$CHF$_2$; —CH$_2$CF$_2$CH$_3$; —CH$_2$CF$_2$CH$_2$F; —CHFCF$_2$CF$_3$;

—CHFCF₂CHF₂; —CHFCF₂CH₃; —CHFCF₂CH₂F; —CF₂CH₂CF₃; —CF₂CH₂CHF₂; —CF₂CH₂CH₃; —CF₂CH₂CH₂F; —CF₂CHFCF₃; —CF₂CHFCHF₂; —CF₂CHFCH₃; —CF₂CHFCH₂F; —CHFCHFCF₃; —CHFCHFCHF₂; —CHFCHFCH₃; —CHFCHFCH₂F; CH₂CH₂CF₃; —CH₂CH₂CHF₂; —CH₂CH₂CH₂F; —CF₂CF₂CF₂CF₃; —CF₂CF₂CF₂CH₃; —CF₂CF₂CF₂CHF₂; —CF₂CF₂CF₂CH₂F; —CH₂CF₂CF₂CF₃; —CH₂CF₂CF₂CH₃; —CH₂CF₂CF₂CHF₂; —CH₂CF₂CF₂CH₂F; —CHFCF₂CF₂CF₃; —CHFCF₂CF₂CH₃; —CHFCF₂CF₂CHF₂; —CHFCF₂CF₂CH₂F; —CF₂CH₂CF₂CF₃; —CF₂CH₂CF₂CH₃; —CF₂CH₂CF₂CHF₂; —CF₂CH₂CF₂CH₂F; —CF₂CHFCF₂CF₃; —CF₂CHFCF₂CH₃; —CF₂CHFCF₂CHF₂; —CF₂CHFCF₂CH₂F; —CHFCHFCF₂CF₃; —CHFCHFCF₂CH₃; —CHFCHFCF₂CHF₂; —CHFCHFCF₂CH₂F; —CH₂CH₂CF₂CF₃; —CH₂CH₂CF₂CH₃; —CH₂CH₂CF₂CHF₂; —CH₂CH₂CF₂CH₂F; —CF₂CF₂CF₂CF₂CF₃; —CH₂CF₂CF₂CF₂CF₃; —CF₂CF₂CF₂ CF₂CHF₂; —CH₂CF₂CF₂ CF₂CHF₂; —CF₂OCFH₂; —CF₂OCF₂H; —CF₂OCF₃; —CF₂OCF₂CF₃; —CF₂OCF₂CHF₂; —CF₂OCF₂CH₃; —CF₂OCF₂CH₂F; —CF₂OCHFCF₃; —CF₂OCHFCHF₂; —CF₂OCHFCH₃; —CF₂OCHFCH₂F; —CF₂OCH₂CF₃; —CF₂OCH₂CHF₂; —CF₂OCH₂CH₂F; —CH₂OCFH₂; —CH₂OCF₂H; —CH₂OCF₃; —CH₂OCF₂CF₃; —CH₂OCF₂CHF₂; —CH₂OCF₂CH₃; —CH₂OCF₂CH₂F; —CH₂OCHFCF₃; —CH₂OCHFCHF₂; —CH₂OCHFCH₃; —CH₂OCHFCH₂F; —CH₂OCH₂CF₃; —CH₂OCH₂CHF₂; —CH₂OCH₂CH₂F; —CHFOCFH₂; —CHFOCF₂H; —CHFOCF₃; —CHFOCF₂CF₃; —CHFOCF₂CHF₂; —CHFOCF₂CH₃; —CHFOCF₂CH₂F; —CHFOCHFCF₃; —CHFOCHFCHF₂; —CHFOCHFCH₃; —CHFOCHFCH₂F; —CHFOCH₂CF₃; —CHFOCH₂CHF₂; or —CHFOCH₂CH₂F. In some embodiments, R⁴, R⁵, R⁶, and R⁷ are individually —CFH₂; —CF₂H; —CF₃; —CF₂CF₃; —CF₂CHF₂; —CF₂CH₃; —CF₂CH₂F; —CHFCF₃; —CHFCHF₂; —CHFCH₃; —CHFCH₂F; —CH₂CF₃; —CH₂CHF₂; —CH₂CH₂F; —CF(CF₃)₂; —CH(CF₃)₂; —CF₂CF₂CF₃; —CF₂CF₂CHF₂; —CF₂CF₂CH₃; —CF₂CF₂CH₂F; —CH₂CF₂CF₃; —CH₂CF₂CHF₂; —CH₂CF₂CH₃; —CHFCF₂CF₃; —CHFCF₂CHF₂; —CHFCF₂CH₃; —CHFCF₂CH₂F; or —CF₂CH₂CF₃. In some embodiments, R⁴, R⁵, R⁶, and R⁷ are —CH₂CF₃.

Generally, the fluorinated organosulfate compounds include at least one group selected from alkyl, alkenyl, alkynyl, aryl, heteroaryl, heterocyclyl, aralkyl, or heteroarylalkyl groups that contain at least one fluorine atom. Illustrative examples, of such groups include, but are not limited to —CFH₂; —CF₂H; —CF₃; —CF₂CF₃; —CF₂CHF₂; —CF₂CH₃; —CF₂CH₂F; —CHFCF₃; —CHFCHF₂; —CHFCH₃; —CHFCH₂F; —CH₂CF₃; —CH₂CHF₂; —CH₂CH₂F; —CF(CF₃)₂; —CH(CF₃)₂; —CF₂CF₂CF₃; —CF₂CF₂CHF₂; —CF₂CF₂CH₃; —CF₂CF₂CH₂F; —CH₂CF₂CF₃; —CH₂CF₂CHF₂; —CH₂CF₂CH₃; —CH₂CF₂CH₂F; —CHFCF₂CF₃; —CHFCF₂CHF₂; —CHFCF₂CH₃; —CHFCF₂CH₂F; —CF₂CH₂CF₃; —CF₂CH₂CHF₂; —CF₂CH₂CH₃; —CF₂CH₂CH₂F; —CF₂CHFCF₃; —CF₂CHFCHF₂; —CF₂CHFCH₃; —CF₂CHFCH₂F; —CHFCHFCF₃; —CHFCHFCHF₂; —CHFCHFCH₃; —CH₂CH₂CH₂F; —CH₂CH₂CHF₂; —CH₂CH₂CH₂F; —CF₂CF₂CF₂CF₃; —CF₂CF₂CF₂CHF₂; —CF₂CF₂CF₂CH₃; —CF₂CF₂CF₂CH₂F; —CH₂CF₂CF₂CF₃; —CH₂CF₂CF₂CHF₂; —CH₂CF₂CF₂CH₃; —CH₂CF₂CF₂CH₂F; —CHFCF₂CF₂CF₃; —CHFCF₂CF₂CHF₂; —CHFCF₂CF₂CH₃; —CHFCF₂CF₂CH₂F; —CF₂CH₂CF₂CF₃; —CF₂CH₂CF₂CHF₂; —CF₂CH₂CF₂CH₃; —CF₂CH₂CF₂CH₂F; —CF₂CHFCF₂CF₃; —CF₂CHFCF₂CHF₂; —CF₂CHFCF₂CH₃; —CF₂CHFCF₂CH₂F; —CHFCHFCF₂CF₃; —CHFCHFCF₂CHF₂; —CHFCHFCF₂CH₃; —CHFCHFCF₂CH₂F; —CH₂CH₂CF₂CF₃; —CH₂CH₂CF₂CHF₂; —CH₂CH₂CF₂CH₃; —CH₂CH₂CF₂CH₂F; —CF₂CF₂CF₂CF₂CF₃; —CH₂CF₂CF₂CF₂CF₃; —CF₂CF₂CF₂CF₂CHF₂; —CH₂CF₂CF₂CF₂CHF₂; —OCFH₂; —OCF₂H; —OCF₃; —OCF₂CF₃; —OCF₂CHF₂; —OCF₂CH₃; —OCF₂CH₂F; —OCHFCF₃; —OCHFCHF₂; —OCHFCH₃; —OCHFCH₂F; —OCH₂CF₃; —OCH₂CHF₂; —OCH₂CH₂F; CF₂OCFH₂; —CF₂OCF₂H; —CF₂OCF₃; —CF₂OCF₂CF₃; —CF₂OCF₂CHF₂; —CF₂OCF₂CH₃; —CF₂OCF₂CH₂F; —CF₂OCHFCF₃; —CF₂OCHFCHF₂; —CF₂OCHFCH₃; —CF₂OCHFCH₂F; —CF₂OCH₂CF₃; —CF₂OCH₂CHF₂; —CF₂OCH₂CH₂F; —CH₂OCFH₂; —CH₂OCF₂H; —CH₂OCF₃; —CH₂OCF₂CF₃; —CH₂OCF₂CHF₂; —CH₂OCF₂CH₃; —CH₂OCF₂CH₂F; —CH₂OCHFCF₃; —CH₂OCHFCHF₂; —CH₂OCHFCH₃; —CH₂OCHFCH₂F; —CH₂OCH₂CF₃; —CH₂OCH₂CHF₂; —CH₂OCH₂CH₂F; —CHFOCFH₂; —CHFOCF₂H; —CHFOCF₃; —CHFOCF₂CF₃; —CHFOCF₂CHF₂; —CHFOCF₂CH₃; —CHFOCF₂CH₂F; —CHFOCHFCF₃; —CHFOCHFCHF₂; —CHFOCHFCH₃; —CHFOCHFCH₂F; —CHFOCH₂CF₃; —CHFOCH₂CHF₂; —CHFOCH₂CH₂F; an mixtures of any two or more thereof.

In any of the above embodiments regarding Formula II, x is 1, or x is 2.

In any of the above embodiments, the electrolyte may include a compound of Formula I, Formula II, or a mixture of any two or more thereof:

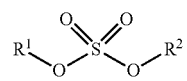

Formula I

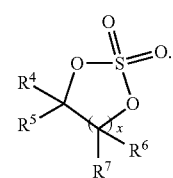

Formula II

In the Formulae, R¹ is alkyl, R³O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy; R² is alkyl, R³O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy; R³ is H, alkyl, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy; x is 1 or 2; R⁴ is H, F, OR⁸, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR⁸, —OC(O)R⁸; R⁵ is H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR$^8$, —OC(O)R$^8$; each R$^6$ is individually H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, —C(O)OR$^8$, —OC(O)R$^8$; each R$^7$ is individually H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, —OC(O)R$^8$; or wherein R$^4$ and R$^5$ or R$^6$ and R$^7$ join together to form an =O group; each R$^8$ is individually H, alkyl, alkenyl, aralkyl, polyalkylene glycol, or silyl; and at least one of R$^1$ and R$^2$ in Formula I is a fluorinated group, and/or at least one of R$^4$, R$^5$, R$^6$, or R$^7$ in Formula II is fluorine or is a fluorinated group.

In any of the above electrolytes, the electrolyte may include the salt, an aprotic solvent, and any of the fluorinated organosulfate compounds as described herein. The fluorinated organosulfate compound may be present in the non—aqueous electrolyte from about 0.01 wt % to about 10 wt %.

The electrolytes as described above may further include a non—aqueous solvent. Illustrative non-aqueous solvents include, but are not limited to, but are not limited to ethylene carbonate, dimethyl carbonate, ethyl methyl carbonate, diethyl carbonate, propylene carbonate, fluorinated carbonates, fluoroethylene carbonate, 4-(trifluoromethyl)-1,3-dioxolan-2-one, propylene carbonate, dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, dimethoxyethane, triglyme, dimethyl ether, diglyme, tetraglyme, dimethyl ethylene carbonate, ethyl acetate, trifluoroethyl acetate, ethyl methyl sulfone, sulfolane, methyl isopropyl sulfone, butyrolactone, acetonitrile, succinonitrile, methyl 2-cyanoacetate, N,N-dimethylacetamide, 2,2,2-trifluoro-N,N-dimethylacetamide, methyl dimethylcarbamate, 2,2,2-trifluoroethyl dimethylcarbamate, or a mixture of any two or more thereof. Other solvents that may be used in the electrolytes include, but are not limited to, organic sulfates, esters, cyclic esters, fluorinated esters, nitriles, amides, dinitriles, fluorinated amides, carbamates, fluorinated carbamates, cyanoester compounds, and ionic liquid such as pyrrolidinium-based ionic liquids, piperidinium-based ionic liquids, imidazolium-based ionic liquids, ammonium-based ionic liquids, phosphonium-based ionic liquids, cyclic phosphonium-based ionic liquids, and sulfonium-based ionic liquids. In some embodiments, the solvents are ether-based solvents. Illustrative ether-based solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), (2,2,2-trifluoroethyl) carbonate (FEMC), 1,4-dioxane, 1,1,2,2-tetrafluoroethyl-2,2,3,3-tetrafluoropropyl ether; 1,1,2,2-tetrafluoroethyl-2,2,3,3,3-pentafluoropropyl ether; 2,2,2-trisfluoroethyl-1,1,2,3,3,3-hexafluoropropyl ether; ethyl-1,1,2,3,3,3-hexafluoropropyl ether; difluoromethyl-2,2,3,3,3-pentafluoropropyl ether; difluoromethyl-2,2,3,3—tetrafluoropropyl ether; 2-fluoro-1,3-dioxolane; 2,2-difluoro-1,3-dioxolane; 2-trifluoromethyl-1,3-dioxolane; 2,2-bis(trifluoromethyl)-1,3-dioxolane; 4-fluoro-1,3-dioxolane; 4,5-difluoro-1,3-dioxolane, or a mixture of any two or more. In some embodiments, the solvents may be carbonated-based solvents, ether-based solvents, fluorinated ether-based solvents, dimethyl sulfoxide, sulfone, ionic liquids, or a mixture of any two or more thereof. In some embodiments, the non-aqueous solvents are non-fluorinated, non-aqueous solvents. Illustrative non-fluorinated, non-aqueous solvents include, but are not limited to, ethylene carbonate, dimethyl carbonate, ethyl methyl carbonate, diethyl carbonate, propylene carbonate, fluorinated carbonate, or a mixture of any two or more thereof. In some embodiments, the co-solvents are ether-based solvents. Illustrative ether-based co-solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra(ethylene glycol) dimethyl ether ("TEGDME"), poly (ethylene glycol) dimethyl ether (PEGDME), 1,4-dioxane, or a mixture of any two or more thereof.

In embodiments where the electrolytes alone, or as part of the electrochemical device, or otherwise, includes a non-aqueous and/or non-fluorinated solvent, the compound of Formula I, Formula II, or mixture of any two or more thereof may be present in the non-aqueous solvent from about 0.01 wt % to about 50 wt %. This may include from about 0.01 wt % to about 20 wt %, from about 0.1 wt % to about 40 wt %, from about 1 wt % to about 40 wt %, from about 5 wt % to about 50 wt %, from about 5 wt % to about 25 wt %, from about 0.01 wt % to about 5 wt %, from about 0.1 wt % to about 5 wt %, or from about 0.01 wt % to about 1 wt %.

Illustrative fluorinated solvents include, but are not limited to, fluorinated carbonates, fluorinated ethers, fluorinated esters, fluorinated amides, and fluorinated carbamates. Non-limiting examples include, but are not limited to, fluoroethylene carbonate, difluoroethylene carbonate, 4-(trifluoromethyl)-1,3-dioxolan-2-one, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, trifluoroethyl acetate, 2,2,2-trifluoro-N,N-dimethylacetamide, 2,2,2-trifluoroethyl dimethylcarbamate, or a mixture of any two or more thereof.

As noted, the electrolytes also include a salt. The salt may include lithium salts, sodium salts, or ammonium salts. The salt may a lithium salt that includes a lithium alkyl fluorophosphate; a lithium alkyl fluoroborate; lithium 4,5-dicyano-2-(trifluoromethyl)imidazole; lithium 4,5-dicyano-2-methylimidazole; trilithium 2,2',2"-tris(trifluoromethyl)benzotris(imidazolate); Li(CF$_3$CO$_2$); Li(C$_2$F$_5$CO$_2$); LiCF$_3$SO$_3$; LiCH$_3$SO$_3$; LiN(SO$_2$CF$_3$)$_2$; LiC(CF$_3$SO$_2$)$_3$; LiN(SO$_2$C$_2$F$_5$)$_2$; LiClO$_4$; LiBF$_4$; LiAsF$_6$; LiPF$_6$; LiPF$_2$(C$_2$O$_4$)$_2$; LiPF$_4$(C$_2$O$_4$); LiB(C$_2$O$_4$)$_2$; LiBF$_2$(C$_2$O$_4$)$_2$; Li$_2$(B$_{12}$X$_{12-n}$H$_n$); Li$_2$(B$_{10}$X$_{10-n'}$); or a mixture of any two or more thereof, wherein X is independently at each occurrence a halogen, n is an integer from 0 to 12, and n' is an integer from 0 to 10.

The salt may be a sodium salt that includes a Na(CF$_3$CO$_2$); Na(C$_2$F$_5$CO$_2$); NaClO$_4$; NaBF$_4$; NaAsF$_6$; NaPF$_6$; NaPF$_2$(C$_2$O$_4$)$_2$; NaPF$_4$(C$_2$O$_4$); NaCF$_3$SO$_3$; NaCH$_3$SO$_3$; NaN(SO$_2$CF$_3$)$_2$; NaC(CF$_3$SO$_2$)$_3$; NaN(SO$_2$C$_2$F$_5$)$_2$; a sodium alkyl fluorophosphate; a sodium alkyl fluoroborate; sodium 4,5-dicyano-2-(trifluoromethyl)imidazole; sodium 4,5-dicyano-2-methylimidazole; trisodium 2,2',2"-tris(trifluoromethyl)benzotris(imidazolate); NaB $(C_2O_4)_2$; $NaBF_2(C_2O_4)_2$; $Na_2(B_{12}X_{12-n'}H_{n'})$; $Na_2(B_{10}X_{10-n'}H_{n'})$; or a mixture of any two or more thereof, wherein X is independently at each occurrence a halogen, n, is an integer from 0 to 12 and n' is an integer from 0 to 10.

The electrolytes as described herein may further include an aprotic gel polymer carrier/solvent. Illustrative gel polymer carrier/solvents include, but are not limited to, polyacrylonitrile, poly(ethylene glycol), poly(vinylidene fluoride), and other polymers which have been swollen with the non-aqueous electrolysis solution having a lithium salt dissolved therein.

The electrolytes as described herein may further include an electrode stabilizing additive or redox shuttle molecules for overcharge protection. Illustrative electrode stabilizing additive or redox shuttle molecules for overcharge protection include, but are not limited to, a spirocyclic hydrocarbon containing at least one oxygen atom and at least on alkenyl or alkynyl group, pyridazine, anisoles, 2,5-dimethyl-1,4-dimethoxybenzene, 2,3,5,6-tetramethyl-1,4-dimethoxybenzene, 2,5-di-tert-butyl-1,4-dimethoxybenzene, vinyl pyridazine, quinolone, pyridine, vinyl pyridine, 2,4-divinyltetrahydrooyran, 3,9-diethylidene-2,4,8-trioxaspiro[5,5]undecane, 2-ethylidene-5-vinyl-[1,3]dioxane, or a mixture of two or more thereof.

In another aspect, an electrochemical device is provided that includes any of the above electrolytes having a fluorinated organosulfate compound, a cathode, and an anode. Such electrochemical devices may also include a separator between the anode and cathode. As used herein, the term "electrochemical device" includes, but is not limited to, primary batteries, secondary batteries, double layer capacitors, pseudo-capacitors, electrolytic cells and fuel cells. Such electrochemical devices may be a lithium-ion secondary battery, a lithium-sulfur secondary battery, a lithium-air secondary battery, a sodium-ion secondary battery, a sodium-sulfur secondary battery, or a sodium-air secondary battery. In such devices, it is believed that the fluorinated organosulfate compounds may form stable SEI films on the surface of the anode to impart stable cycling performance. In some embodiments, the device is a high voltage battery operating at a voltage of greater than 4.4 V. This may include voltages of greater than 4.4 V to about 4.7 V. Where the battery is a lithium-ion battery the voltage is versus $Li/Li^+$, and where the battery is a sodium-ion battery the voltage is versus $Na/Na^+$.

The cathode of the electrochemical devices described herein may include a spinel, an olivine, a surface modified olivine $LiFePO_4$, $LiMn_{0.5}Ni_{0.5}O_2$, $LiCoO_2$, $LiNiO_2$, $LiNi_{1-x}Co_yMe_zO_2$, $LiNi_\alpha Mn_\beta Co_\gamma O_2$, $LiMn_2O_4$, $LiFeO_2$, $LiNi_{0.5}Me_{1.5}O_4$, $Li_{1+x}Ni_hMn_kCoN_1Me^2_{y'}O_{2-z'}F_{z'}$, $VO_2$, $E_xF_2(Me_3O_4)_3$, or $LiNi_mMn_nO_4$, wherein Me is Al, Mg, Ti, B, Ga, Si, Mn, or Co; $Me^2$ is Mg, Zn, Al, Ga, B, Zr, or Ti; E is Li, Ag, Cu, Na, Mn, Fe, Co, Ni, or Zn; F is Ti, V, Cr, Fe, or Zr; wherein $0 \le x \le 0.3$; $0 \le y \le 0.5$; $0 \le z \le 0.5$; $0 \le m \le 2$; $0 \le n \le 2$; $0 \le x' \le 0.4$; $0 \le \alpha < 1$; $0 \le \beta \le 1$; $0 \le \gamma \le 1$; $0 \le h \le 1$; $0 \le k < 1$; $0 \le l \le 1$; $0 \le y' \le 0.4$; $0 \le z' \le 0.4$; and $0 \le x'' \le 3$; with the proviso that at least one of h, k and 1 is greater than 0.

The term "spinel" refers to a manganese-based spinel such as, $Li_{1+x}Mn_{2-y}Me_zO_{4-h}A_k$, wherein Me is Al, Mg, Ti, B, Ga, Si, Ni, or Co; A is S or F; and wherein $0 \le x \le 0.5$, $0 \le y \le 0.5$, $0 \le z \le 0.5$, $0 \le h \le 0.5$, and $0 \le k \le 0.5$.

The term "olivine" refers to an iron-based olivine such as, $LiFe_{1-x}Me_yPO_{4-h}A_k$, wherein Me is Al, Mg, Ti, B, Ga, Si, Ni, or Co; A is S or F; and wherein $0 \le x \le 0.5$, $0 \le y \le 0.5$, $0 \le h \le 0.5$, and $0 \le k \le 0.5$.

In some embodiments, the cathode includes a layered structure, a spinel, a olivine with and without coating material that includes, but is not limited to carbon, polymer, fluorine, metal oxides, $NaFePO_4$, $NaCoO_2$, $NaNiO_2$, $NaMn_2O_4$, or $Na_{1-x}Ni_\alpha Co_\beta Mn_\gamma M_{67}O_{2-z}N_z$, wherein M is Li, Al, Mg, Ti, B, Ga, Si, Zr, Zn, Cu, Fe; N is F, Cl, S; wherein $0 \le x \le 1$, $0 \le \alpha \le 1$, $0 \le \beta \le 1$, $0 \le \gamma \le 1$, $0 \le \delta \le 1$, $0 \le z \le 2$; with the proviso that at least one of α, β and γ is greater than 0. In some embodiments, the positive electrode includes $Li_{1+w}Mn_xNi_yCo_zO_2$ wherein w, x, y, and z satisfy the relations $0 \le w \le 1$, $0 \le x \le 1$, $0 \le y \le 1$, $0 \le z \le 1$, and $x+y+z=1$. In some embodiments, the cathode may be intercalated with lithium.

In some embodiments, the cathode includes $LiMn_xNi_yO_4$ wherein x and y satisfy the $0 \le x < 2$, $0 \le y \le 2$ and $x+y=2$. In some embodiments, the cathode includes $LiMn_xNi_yO_4$ wherein x and y satisfy the $0 \le x \le 2$, 0 and $x+y=2$. In some embodiments, the cathode includes $xLi_2MnO_3 \cdot (1-x)LiMO_2$ is wherein $0 \le x \le 2$.

In some embodiments, the cathode includes $Na_wMn_xNi_yCo_zO_2$ wherein w, x, y, and z satisfy the relations $0 \le w \le 1.5$, $0 \le x < 1$, $0 \le y \le 1$, $0 \le z \le 1$, and $x+y+z=1$.

In some embodiments, the cathode includes $Na_wMe_xO_2$ wherein Me is any transition metal and w and x satisfy the relations $0 < w < 1.5$, $0 \le x \le 1$.

The cathode may be further stabilized by surface coating the active particles with a material that can neutralize acid or otherwise lessen or prevent leaching of the transition metal ions. For example, the cathodes may include a surface coating of a metal oxide or fluoride such as $ZrO_2$, $TiO_2$, $ZnO_2$, $WO_3$, $Al_2O_3$, $MgO$, $SiO_2$, $SnO_2$, $AlPO_4$, $Al(OH)_3$, $AlF_3$, $ZnF_2$, $MgF_2$, $TiF_4$, $ZrF_4$, $LiMPO_4$ or $LiMBO_3$, where in M indicates transition metal such as but not limited to Ni, Mn, Co a mixture of any two or more thereof, of any other suitable metal oxide or fluoride. The coating can be applied to a carbon coated cathode.

The cathode may be further stabilized by surface coating the active particles with polymer materials. Examples of polymer coating materials include, but not limited to, polysiloxanes, polyethylene glycol, or poly(3,4-ethylenedioxythiophene)polystyrene sulfonate, a mixture of any two or more polymers.

The anode of the electrochemical devices described herein may include natural graphite, synthetic graphite, hard carbon, amorphous carbon, soft carbon, mesocarbon microbeads (MCMB), acetylene black, Ketjen black, carbon black, mesoporous carbon, porous carbon matrix, carbon nanotube, carbon nanofiber, graphene, silicon microparticle, silicon nanoparticle, silicon-carbon composite, tin microparticle, tin nanoparticle, tin-carbon composite, silicon-tin composite, phosphorous-carbon composites, black phosphorus, red phosphorus, mixture of red and black phosphorus, lithium titanium oxide, lithium metal, sodium metal, lithium titanium oxide or magnesium metal. In some embodiments, the anode includes synthetic graphite, natural graphite, amorphous carbon, hard carbon, soft carbon, acetylene black, MCMB, carbon black, Ketjen black, mesoporous carbon, porous carbon matrix, carbon nanotube, carbon nanofiber, graphene, black phosphorus, red phosphorus, mixture of red and black phosphorus, Ge, SnSb, $NiCo_2O_4$, $Sb_2O_4$, or $Co_3O_4$. In some embodiments, the anode may include a carbon-based material that is intercalated with lithium or sodium, or is alloyed with lithium or sodium metal. In some embodiments, the anode is comprised of particles of the described materials, and the particles are microparticles or nanoparticles. In some embodiments, the negative electrode includes hard carbon or phosphorus-carbon composites or sodium metal or organosodium compound. In some embodiments, the particles are microparticles or nanoparticles.

The anode may be further stabilized by surface coating the active particles with a material. Hence the anodes can also comprise a surface coating of a metal oxide or fluoride such as $ZrO_2$, $TiO_2$, $ZnO_2$, $WO_3$, $Al_2O_3$, MgO, $SiO_2$, $SnO_2$, $AlPO_4$, $Al(OH)_3$, $AlF_3$, $ZnF_2$, $MgF_2$, $TiF_4$, $ZrF_4$, a mixture of any two or more thereof, of any other suitable metal oxide or fluoride.

The anode may be further stabilized by surface coating the active particles with polymer materials. Examples of polymer coating materials include, but not limited to, polysiloxanes, polyethylene glycol, or poly(3,4-ethylenedioxythiophene)polystyrene sulfonate, a mixture of any two or more polymers.

The cathodes and anodes of the electrochemical devices may also include a current collector. The current collector has an obverse surface and a reverse surface. Where the anodic material may be associated with either the obverse or the reverse surface, or both the designation is used to illustrate placement of the lithium/sodium additive material, where the material is lithium metal foil, sodium metal foil, lithium metal particles, or sodium metal particles. For example, where the anodic material is in contact with the obverse surface, the lithium/sodium metal foil, particulate, or powder may be proximal to the reverse surface. Or, in other words, on the opposite face of the current collector from the anodic material. Alternatively, where the anodic material is in contact with the obverse surface, the lithium metal foil may be proximal to the anodic material. Or, in other words, sandwiched between the anodic material and a separator prior to the cathode. The current collectors for either the anode or the cathode may include those of copper, stainless steel, titanium, tantalum, platinum, gold, aluminum, nickel, cobalt, cobalt nickel alloy, highly alloyed ferritic stainless steel containing molybdenum and chromium; or nickel-, chromium-, or molybdenum containing alloys.

The electrodes (i.e., the cathode and/or the anode) may also include a conductive polymer. Illustrative conductive polymers include, but not limited to, polyaniline, polypyrrole, poly(pyrrole-co-aniline), polyphenylene, polythiophene, polyacetylene, polysiloxane, or polyfluorene.

The positive and negative electrodes (cathodes and anodes, respectively) may also include a binder to hold the electroactive materials in the electrode together and to a current collector. Illustrative binders include, but are not limited to, polyvinylidene difluoride (PVDF), poly(acrylic acid) (PAA), lithiated PAA, polyimide (PI), polyacrylonitrile (PAN), styrene-butadiene rubber (SBR), carboxymethyl cellulose (CMC), and combinations of any two or more thereof. Illustrative current collectors, when used, include, but are not limited to, copper, stainless steel, titanium, tantalum, platinum, gold, aluminum, nickel, cobalt-nickel alloys, highly alloyed ferritic stainless steel containing molybdenum and chromium; or nickel-, chromium-, or molybdenum-containing alloys. The current collector may be a foil, mesh, or screen.

As noted above, the electrochemical device disclosed herein may also include a porous separator to separate the cathode from the anode and prevent, or at least minimize, short-circuiting in the device. The separator may be a polymer or ceramic or mixed separator. The separator may include, but is not limited to, polypropylene (PP), polyethylene (PE), trilayer (PP/PE/PP), or polymer films that may optionally be coated with alumina-based ceramic particles.

The present invention, thus generally described, will be understood more readily by reference to the following examples, which are provided by way of illustration and are not intended to be limiting of the present invention.

EXAMPLES

Example 1. 4-(trifluoromethyl)-1,3,2-dioxathiolane 2,2-dioxide ("TFDTD") was synthesized according to Scheme 1.

Scheme 1

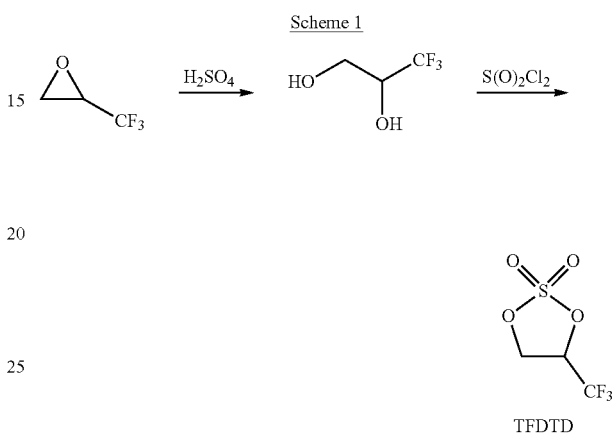

TFDTD 1,1,1-Trifluoro-2,3-epoxypropane was converted to 3,3,3-trifluoropropane-1,2-diol in sulfuric acid solution. The resulting diol was then subject to sulfuryl chloride at −20° C. to room temperature to provide the TFDTD in about 60% yield. After purification by vacuum distillation (96° C., 1 mmHg), the TFDTD was characterized by $^1H$, $^{13}C$, and $^{19}F$ nuclear magnetic resonance (NMR). $^1HNMR$ ($CDCl_3$, 300 MHz): δ 5.21-5.07 (m, 1H), 4.96-4.86 (m, 3H), 4.85-4.75 (m, 1H); $^{13}C$ NMR ($CDCl_3$, 75 MHz): δ 127.0, 123.3, 119.5, 115.9 (q, J=270 Hz), 75.7, 75.2, 74.7, 74.2 (q, J=37.5 Hz), 66.21, 66.18, 66.15, 66.12 (q, 2.3 Hz).

Example 2. Stability testing. Owing to its ability to form SEI on the surface of graphite, organosulfur oxides have been used as electrolyte additives for Li-ion batteries. Various cyclic organosulfur oxides including tetrahydrothiophene 1,1-dioxide (TMS), 1,3,2-dioxathiolane 2-oxide (ES), 1,2-oxathiolane 2,2-dioxide (PS), and 1,3,2-dioxathiolane-2,2-dioxide (ethylene sulfate, DTD) were tested as anode additives in propylene carbonate (PC) electrolyte. The results indicated that the cell employing DTD, which is a cyclic sulfate, displayed good electrochemical performance. Despite its success as graphite additive, DTD is a solid with melting point 96° C., rendering it not feasible to be used as co-solvent in electrolyte. However, the change from DTD to the fluorinated methyl version (TFDTD) lowers the melting point to 96° C. (DTD) to less than 10° C. for the TFDTD.

The stability of the TFDTD is believed to be due to the electron withdrawing effects of the trifluoromethyl group, stabilizing the O—C bond in the ring under acidic conditions. Decomposition of the related DTD and MDTD are shown in Scheme II (note that RDS is an abbreviation for rate-determining step), however due to the electron withdrawing fluorine atoms in TFDTD such decomposition pathways are minimized. Thus, it is a combination of the lack of electron donating substituents on the ring, and the substitution to lower that melting point of the material that is desirable.

Scheme II

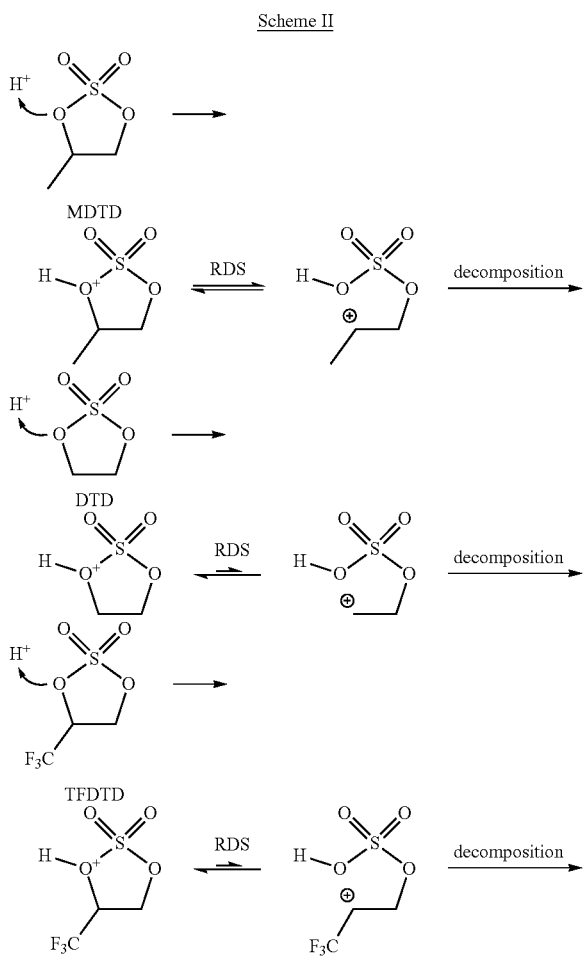

Example 2. A 2032 coin cell was assembled with a cathode of graphite, an anode of lithium metal, and an electrolyte of 1.0M LiPF$_6$ propylene carbonate ("PC"). The coin cell was cycled at a charging rate of C/15. FIG. 1 is a graph illustrating that the co-intercalation of PC with lithium cation at around 0.9V vs. Li$^+$/Li. The electrolyte is unstable due to the lack of robust SEI formation.

Figure 2:
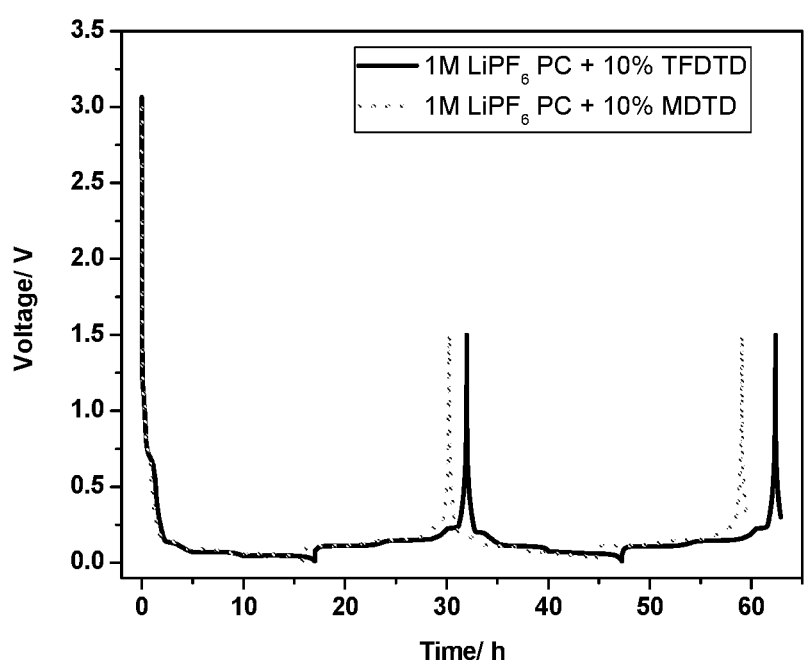
FIG. 2 a graph illustrating the voltage profile of cells using 1.0M LiPF$_6$PC with 10% MDTD and 10% TFDTD using a cathode of graphite, an anode of lithium metal, according to Example 2.

Example 3. FIG. 2 presents the linear sweep voltammetry (LSV) of MDTD- and TFDTD-based electrolytes. The two cells are Al2 graphite/Li cells using electrolytes 1.0M LiPF$_6$ PC with 10 wt. % MDTD and 1.0M LiPF$_6$ PC with 10 wt. % TFDTD. The coin cell was cycled at a charging rate of C/15. With the addition of MDTD or TFDTD, the PC-based electrolyte forms a very stable SEI on the graphite surface, thereby preventing further co-intercalation of PC.

Figure 3:
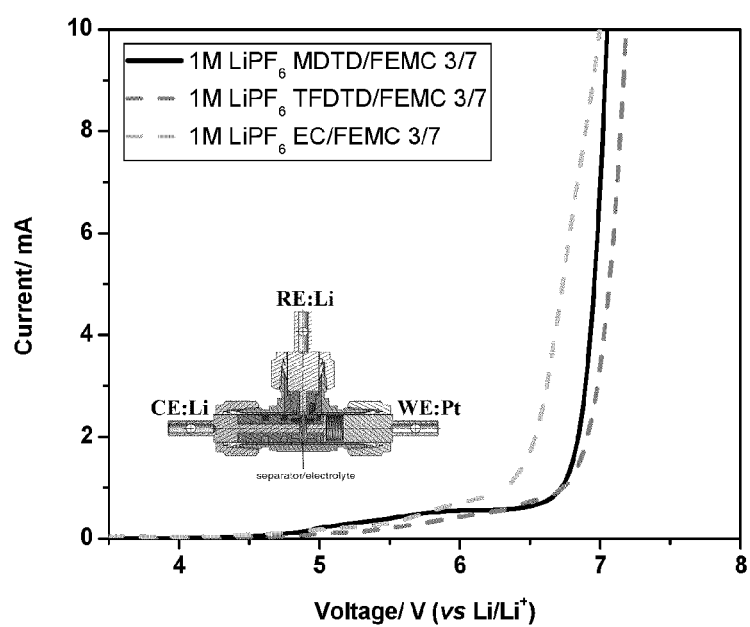
FIG. 3 shows linear sweep voltammograms of 1.0M LiPF$_6$ EC/FEMC (3:7), 1.0M LiPF$_6$ MDTD/FEMC (3:7) and 1.0M LiPF$_6$ TFDTD/FEMC (3:7) using a three-electrode system (Pt working electrode, lithium counter electrode and lithium reference electrode), according to Example 3.

Example 4. FIG. 3 shows the linear sweep voltammograms of electrolytes 1.0M LiPF$_6$ EC/EMC (3:7), 1.0M LiPF$_6$ MDTD/FEMC (3:7) and 1.0M LiPF$_6$ TFDTD/FEMC (3:7) using a three-electrode system (Pt working electrode, lithium counter electrode and lithium reference electrode). For 1.0M LiPF$_6$ EC/EMC (3:7) electrolyte, the oxidation reaction was triggered at about 6.3V vs. Li. For 1.0M LiPF$_6$ MDTD/FEMC (3:7) electrolyte, the oxidation reaction was triggered at about 6.7V vs. Li. For 1.0M LiPF$_6$ TFDTD/FEMC (3:7) electrolyte, the oxidation reaction was triggered at about 6.8V vs. Li. Therefore, the TFDTD—based electrolyte shows the highest anodic stability. FEMC is (2,2,2-trifluoroethyl) carbonate. FEMC was chosen as a co-solvent due to its anodic stability. As shown in FIG. 3, TFDTD based electrolyte began to oxidize at a higher voltage than MDTD based electrolyte, indicating better anodic stability for TFDTD.

Figure 4:
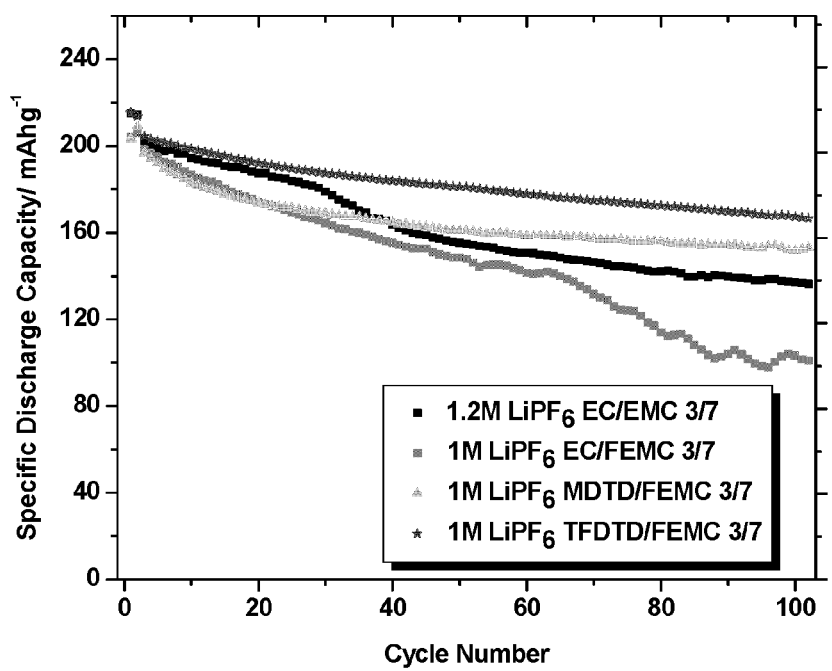
FIG. 4 is a discharge capacity v. cycle number graph for Li$_1$Ni$_{0.5}$Mn$_{0.3}$Co$_{0.2}$O$_2$/A12 graphite 2032 coin cells using 1.2M LiPF$_6$ EC/EMC (3:7), 1.0M LiPF$_6$ EC/FEMC (3:7), 1.0M LiPF$_6$ MDTD/FEMC (3:7) and 1.0M LiPF$_6$ TFDTD/FEMC (3:7) electrolytes, according to Example 4. The cells were cycled from 3.0 V to 4.6 V at a current of C/3.
Figure 5:
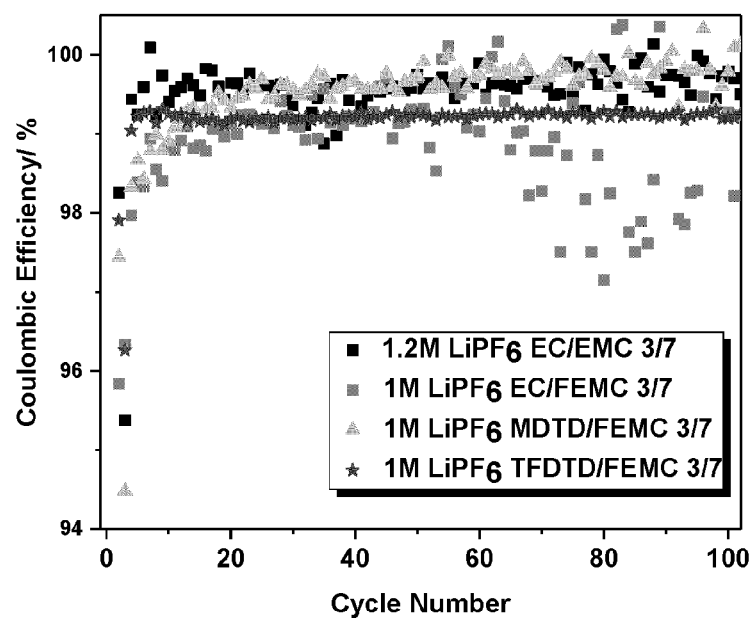
FIG. 5 shows the Coulombic efficiency profiles for A12 graphite/Li$_1$Ni$_{0.5}$Mn$_{0.3}$Co$_{0.2}$O$_2$ 2032 coin cells using 1.2M LiPF$_6$ EC/EMC (3:7), 1.0M LiPF$_6$ EC/FEMC (3:7), 1.0M LiPF$_6$ MDTD/FEMC (3:7) and 1.0M LiPF$_6$ TFDTD/FEMC (3:7) electrolytes, according to Example 4. The cells were cycled from 3.0 V to 4.6 V at a current of C/3.
Figure 6:
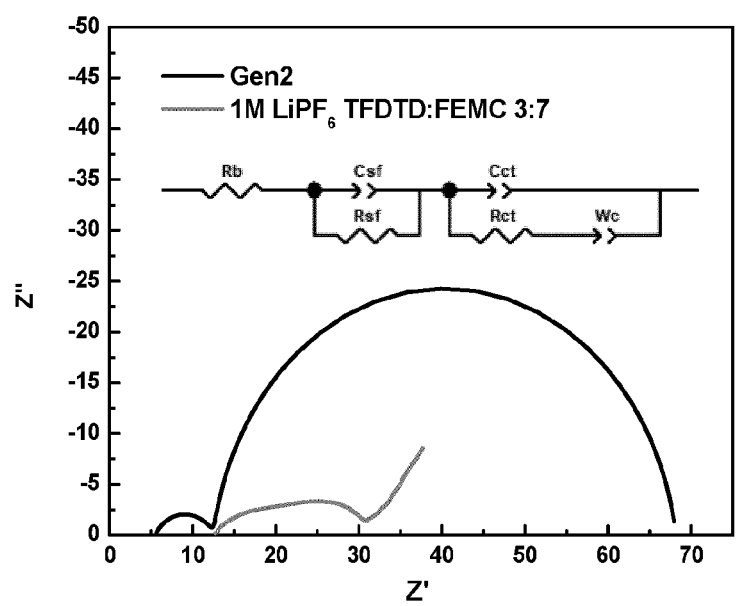
FIG. 6 shows the AC impedance profiles for A12 graphite/Li$_1$Ni$_{0.5}$Mn$_{0.3}$Co$_{0.2}$O$_2$ 2032 coin cells using 1.2M LiPF$_6$ EC/EMC (3:7) and 1.0M LiPF$_6$ TFDTD/FEMC (3:7) electrolytes after 100 cycles, according to Example 5.

Example 5. FIG. 4 shows the discharge capacity of Li$_1$Ni$_{0.5}$Mn$_{0.3}$Co$_{0.2}$O$_2$/A12 graphite 2032 coin cells using 1.2M LiPF$_6$ EC/EMC (3:7), 1.0M LiPF$_6$ EC/FEMC (3:7), 1.0M LiPF$_6$ MDTD/FEMC (3:7) and 1.0M LiPF$_6$ TFDTD/FEMC (3:7) electrolytes. The coin cells were cycled from 3.0 V to 4.6 V at a current of C/3. The cell using TFDTD-based electrolyte shows the best capacity retention (81.5% after 100 cycles), while the cell using baseline electrolyte [i.e. 1.2M LiPF$_6$ EC/EMC (3:7)] only has a 67.9% 100 cycle retention. FIG. 6 shows the Coulombic efficiency of the above cells. The above cells all have Coulombic efficiency larger than 99%, except the cell using 1.0M LiPF$_6$ EC/FEMC (3:7) electrolyte. It is clear that the cell using 1.0M LiPF$_6$ TFDTD/FEMC (3:7) electrolyte shows marked improvement over the baseline electrolyte.

Example 6. The cells of Example 4 were tested for AC impedance after 100 cycles. The cells were charged to 3.75 V with a constant voltage method to assure the same SOC states. The AC impedance was collected over a frequency range of 10 MHz to 1 MHz. As shown in FIG. 6, the charge transfer resistance of the cell using 1.0M LiPF$_6$ TFDTD/FEMC (3:7) electrolyte is significantly smaller than the charge transfer resistance of the cell using baseline electrolyte.

Figure 7:
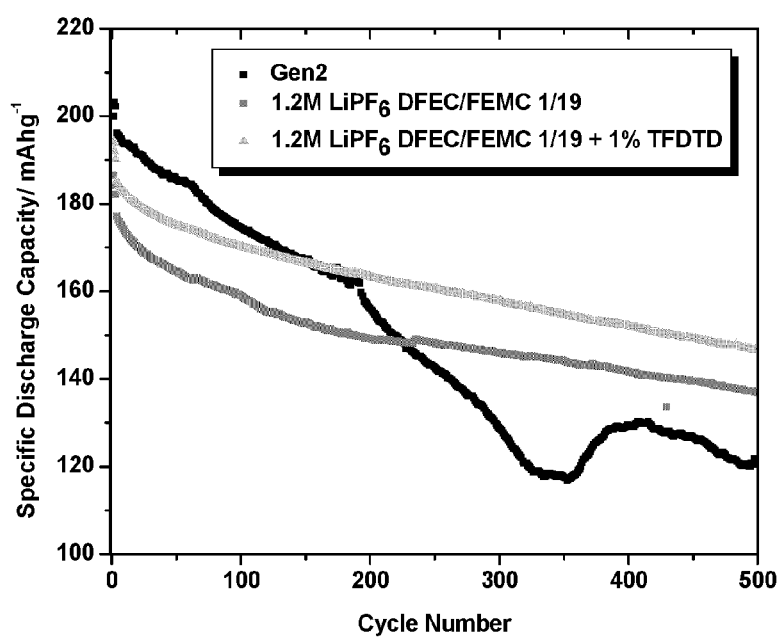
FIG. 7 is a discharge capacity v. cycle number graph for Li$_1$Ni$_{0.6}$Mn$_{0.2}$Co$_{0.2}$O$_2$/A12 graphite 2032 coin cells using 1.2M LiPF$_6$ EC/EMC (3:7), 1.2M LiPF$_6$ DFEC/FEMC (1:19), and 1.2M LiPF$_6$ DFEC/FEMC (1:19) with 1% TFDTD electrolytes, according to Example 6. The cells were cycled from 3.0 V to 4.5 V at a current of C/2.
Figure 8:
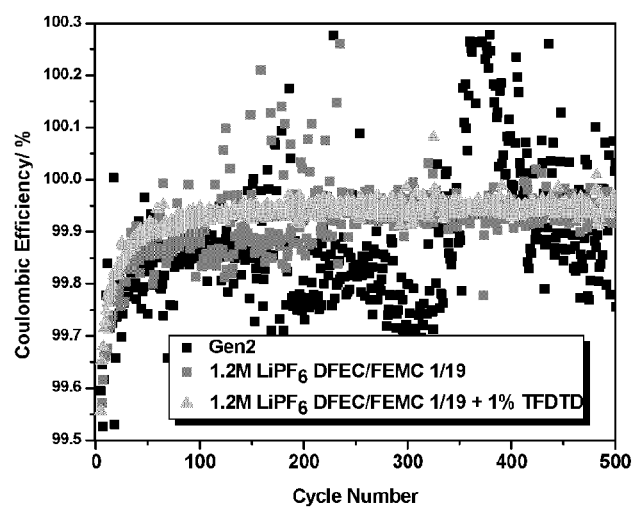
FIG. 8 shows the Coulombic efficiency profiles for Li$_1$Ni$_{0.6}$Mn$_{0.2}$Co$_{0.2}$O$_2$/A22 graphite 2032 coin cells using 1.2M LiPF$_6$ EC/EMC (3:7), 1.2M LiPF$_6$ DFEC/FEMC (1:19), and 1.2M LiPF$_6$ DFEC/FEMC (1:19) with 1% TFDTD electrolytes, according to Example 6. The cells were cycled from 3.0 V to 4.6 V at a current of C/3.

Example 7. FIG. 7 shows the discharge capacity of Li$_1$Ni$_{0.6}$Mn$_{0.2}$Co$_{0.2}$O$_2$/A12 graphite 2032 coin cells using 1.2M LiPF$_6$ EC/EMC (3:7), 1.2M LiPF$_6$ DFEC/FEMC (1:19), and 1.2M LiPF$_6$ DFEC/FEMC (1:19) with 1% TFDTD electrolytes. The coin cells were cycled from 3.0 V to 4.5 V at a current of C/2. The cells using DFEC/FEMC-based electrolyte show much better cycling performance than the cell using baseline electrolyte 1.2M LiPF$_6$ EC/EMC (3:7), while the cell using DFEC/FEMC-based electrolyte with TFDTD additive achieves the best cycling performance. FIG. 8 shows the Coulombic efficiency of the above cells. The above cells all have Coulombic efficiency larger than 99%, especially the cells DFEC/FEMC-based electrolytes have average Coulombic efficiencies larger than 99.9%.

Figure 9:
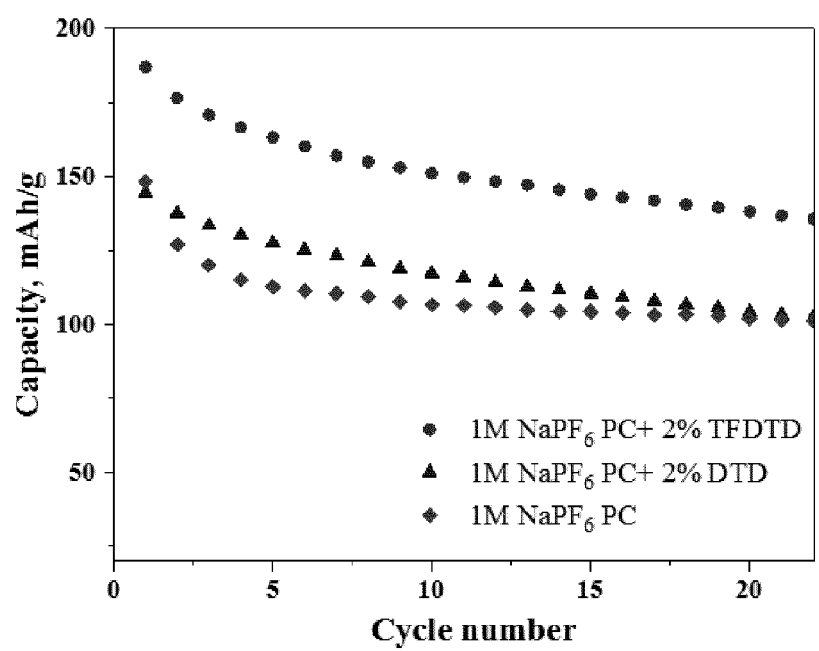
FIG. 9 is a discharge capacity v. cycle number graph for NaMnO$_2$/Na metal 2032 coin cells using 1.0M NaPF$_6$ PC, 1.0M NaPF$_6$ PC with 2% TFDTD and 1.0M NaPF$_6$ PC with 2% DTD electrolytes, according to Example 7. The cells were cycled from 2.0 V to 3.8 V at a current of C/10.
Figure 10:
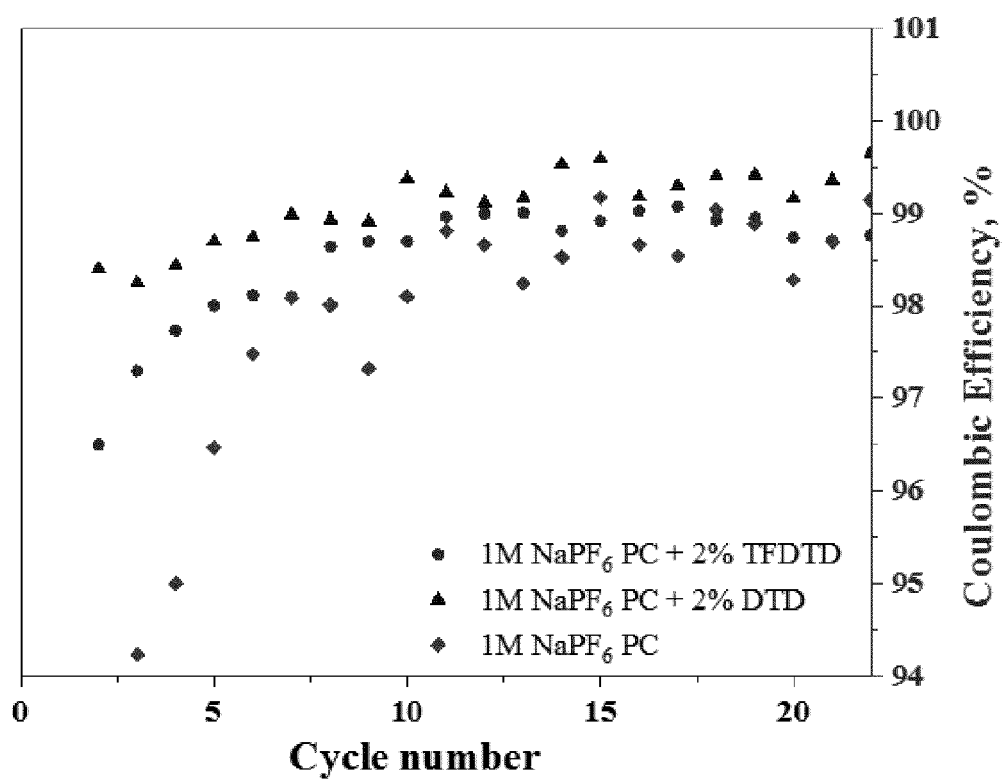
FIG. 10 shows the Coulombic efficiency profiles for NaMnO$_2$/Na metal 2032 coin cells using 1.0M NaPF$_6$ PC, 1.0M NaPF$_6$ PC with 2% TFDTD and 1.0M NaPF$_6$ PC with 2% DTD electrolytes, according to Example 7. The cells were cycled from 2.0 V to 3.8 V at a current of C/10.

Example 8. FIG. 9 shows the discharge capacity of NaMnO$_2$/Na metal 2032 coin cells using 1.0M NaPF$_6$ PC, 1.0M NaPF$_6$ PC with 2% TFDTD and 1.0M NaPF$_6$ PC with 2% DTD electrolytes, according to Example 7. The coin cells were cycled from 2.0 V to 3.8 V at a current of C/10. The cells using electrolytes with DTD or TFDTD additive show better cycling performance than the cell using baseline electrolyte 1.0M NaPF$_6$ PC, while the cell using 1.0M NaPF$_6$ PC with 2% TFDTD additive achieves the best cycling performance. FIG. 10 shows the Coulombic efficiency of the above cells. It is clear that the cells using electrolytes with DTD or TFDTD additives show enhanced Coulombic efficiencies than the cell using baseline electrolyte.

Para. A. An electrolyte comprising:
a salt; and
a fluorinated organosulfate compound represented by Formula I, Formula II, or a
mixture of any two or more thereof:

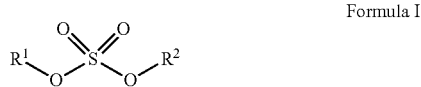

Formula I

-continued

Formula II $$\begin{array}{c} R^4 \\ R^5 \end{array} \begin{array}{c} O \\ \diagdown \\ O \end{array} \begin{array}{c} O \\ \diagup \\ S \end{array} \begin{array}{c} O \\ \diagdown \\ O \end{array}$$
$R^7$ $R^6$ $_x$ wherein:
  R¹ is alkyl, R³O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
  R² is alkyl, R³O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
  R³ is H, alkyl, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
  x is 1 or 2;
  R⁴ is H, F, OR⁸, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR⁸, —OC(O)R⁸;
  R⁵ is H, F, OR⁸, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR⁸, —OC(O)R⁸;
  each R⁶ is individually H, F, OR⁸, alkyl, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, —C(O)OR⁸, —OC(O)R⁸;
  each R⁷ is individually H, F, OR⁸, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR⁸, —OC(O)R⁸;
  or wherein R⁴ and R⁵ or R⁶ and R⁷ join together to form an =O group;
  each R⁸ is individually H, alkyl, alkenyl, aralkyl, polyalkylene glycol, or silyl; and
  at least one of R¹ and R² in Formula I is a fluorinated group, and/or at least one of R⁴, R⁵, R⁶, or R⁷ in Formula II is fluorine or is a fluorinated group.

Para. B. The electrolyte of Para. A, wherein at least one of R¹ and R² is —CFH₂; —CF₂H; —CF₃; —CF₂CF₃; —CF₂CHF₂; —CF₂CH₃; —CF₂CH₂F; —CHFCF₃; —CHFCHF₂; —CHFCH₃; —CHFCH₂F; —CH₂CF₃; —CH₂CHF₂; —CH₂CH₂F; —CF(CF₃)₂; —CH(CF₃)₂; —CF₂CF₂CF₃; —CF₂CF₂CHF₂; —CF₂CF₂CH₃; —CF₂CF₂CH₂F; —CH₂CF₂CF₃; —CH₂CF₂CHF₂; —CH₂CF₂CH₃; —CH₂CF₂CH₂F; —CHFCF₂CF₃; —CHFCF₂CHF₂; —CHFCF₂CH₃; —CHFCF₂CH₂F; —CF₂CH₂CF₃; —CF₂CH₂CHF₂; —CF₂CH₂CH₃; —CF₂CH₂CH₂F; —CF₂CHFCF₃; —CF₂CHFCHF₂; —CF₂CHFCH₃; —CF₂CHFCH₂F; —CHFCHFCF₃; —CHFCHFCHF₂; —CHFCHFCH₃; —CHFCHFCH₂F; CH₂CH₂CF₃; —CH₂CH₂CHF₂; —CH₂CH₂CH₂F; —CF₂CF₂CF₂CF₃; —CF₂CF₂CF₂CH₃; —CF₂CF₂CF₂CHF₂; —CF₂CF₂CF₂CH₂F; —CH₂CF₂CF₂CF₃; —CH₂CF₂CF₂CHF₂; —CH₂CF₂CF₂CH₃; —CH₂CF₂CF₂CH₂F; —CHFCF₂CF₂CF₃; —CHFCF₂CF₂CH₃; —CHFCF₂CF₂CHF₂; —CHFCF₂CF₂CH₂F; —CF₂CH₂CF₂CF₃; —CF₂CH₂CF₂CH₃; —CF₂CH₂CF₂CHF₂; —CF₂CH₂CF₂CH₂F; —CF₂CHFCF₂CF₃; —CF₂CHFCF₂CH₃; —CF₂CHFCF₂CHF₂; —CF₂CHFCF₂CH₂F; —CHFCHFCF₂CF₃; —CHFCHFCF₂CH₃; —CHFCHFCF₂CHF₂; —CHFCHFCF₂CH₂F; —CH₂CH₂CF₂CF₃; —CH₂CH₂CF₂CH₃; —CH₂CH₂CF₂CHF₂; —CH₂CH₂CF₂CH₂F; —CF₂CF₂CF₂CF₂CF₃; —CH₂CF₂CF₂CF₂CF₃; —CF₂CF₂CF₂ CF₂CHF₂; —CH₂CF₂CF₂ CF₂CHF₂; —CF₂OCFH₂; —CF₂OCF₂H; —CF₂OCF₃; —CF₂OCF₂CF₃; —CF₂OCF₂CHF₂; —CF₂OCF₂CH₃; —CF₂OCF₂CH₂F; —CF₂OCHFCF₃; —CF₂OCHFCHF₂; —CF₂OCHFCH₃; —CF₂OCHFCH₂F; —CF₂OCH₂CF₃; —CF₂OCH₂CHF₂; —CF₂OCH₂CH₂F; —CH₂OCFH₂; —CH₂OCF₂H; —CH₂OCF₃; —CH₂OCF₂CF₃; —CH₂OCF₂CHF₂; —CH₂OCF₂CH₃; —CH₂OCF₂CH₂F; —CH₂OCHFCF₃; —CH₂OCHFCHF₂; —CH₂OCHFCH₃; —CH₂OCHFCH₂F; —CH₂OCH₂CF₃; —CH₂OCH₂CHF₂; —CH₂OCH₂CH₂F; —CHFOCFH₂; —CHFOCF₂H; —CHFOCF₃; —CHFOCF₂CF₃; —CHFOCF₂CHF₂; —CHFOCF₂CH₃; —CHFOCF₂CH₂F; —CHFOCHFCF₃; —CHFOCHFCHF₂; —CHFOCHFCH₃; —CHFOCHFCH₂F; —CHFOCH₂CF₃; —CHFOCH₂CHF₂; or —CHFOCH₂CH₂F.

Para. C. The electrolyte of Para. A or B, wherein at least one of R⁴, R⁵, R⁶, or R⁷ is F; —CFH₂; —CF₂H; —CF₃; —CF₂CF₃; —CF₂CHF₂; —CF₂CH₃; —CF₂CH₂F; —CHFCF₃; —CHFCHF₂; —CHFCH₃; —CHFCH₂F; —CH₂CF₃; —CH₂CHF₂; —CH₂CH₂F; —CF(CF₃)₂; —CH(CF₃)₂; —CF₂CF₂CF₃; —CF₂CF₂CHF₂; —CF₂CF₂CH₃; —CF₂CF₂CH₂F; —CH₂CF₂CF₃; —CH₂CF₂CHF₂; —CH₂CF₂CH₃; —CH₂CF₂CH₂F; —CHFCF₂CF₃; —CHFCF₂CHF₂; —CHFCF₂CH₃; —CHFCF₂CH₂F; —CF₂CH₂CF₃; —CF₂CH₂CHF₂; —CF₂CH₂CH₃; —CF₂CH₂CH₂F; —CF₂CHFCF₃; —CF₂CHFCHF₂; —CF₂CHFCH₃; —CF₂CHFCH₂F; —CHFCHFCF₃; —CHFCHFCHF₂; —CHFCHFCH₃; —CHFCHFCH₂F; CH₂CH₂CF₃; —CH₂CH₂CHF₂; —CH₂CH₂CH₂F; —CF₂CF₂CF₂CF₃; —CF₂CF₂CF₂CH₃; —CF₂CF₂CF₂CHF₂; —CF₂CF₂CF₂CH₂F; —CH₂CF₂CF₂CF₃; —CH₂CF₂CF₂CHF₂; —CH₂CF₂CF₂CH₃; —CH₂CF₂CF₂CH₂F; —CHFCF₂CF₂CF₃; —CHFCF₂CF₂CH₃; —CHFCF₂CF₂CHF₂; —CHFCF₂CF₂CH₂F; —CF₂CH₂CF₂CF₃; —CF₂CH₂CF₂CH₃; —CF₂CH₂CF₂CHF₂; —CF₂CH₂CF₂CH₂F; —CF₂CHFCF₂CF₃; —CF₂CHFCF₂CH₃; —CF₂CHFCF₂CHF₂; —CF₂CHFCF₂CH₂F; —CHFCHFCF₂CF₃; —CHFCHFCF₂CH₃; —CHFCHFCF₂CHF₂; —CHFCHFCF₂CH₂F; —CH₂CH₂CF₂CF₃; —CH₂CH₂CF₂CH₃; —CH₂CH₂CF₂CHF₂; —CH₂CH₂CF₂CH₂F; —CF₂CF₂CF₂CF₂CF₃; —CH₂CF₂CF₂CF₂CF₃; —CF₂CF₂CF₂ CF₂CHF₂; —CH₂CF₂CF₂CF₂CHF₂; —OCFH₂; —OCF₂H; —OCF₃; OCF₂CF₃; —OCF₂CHF₂; —OCF₂CH₃; OCF₂CH₂F; —OCHFCF₃; —OCHFCHF₂; —OCHFCH₃; —OCHFCH₂F; —OCH₂CF₃; —OCH₂CHF₂; —OCH₂CH₂F; CF₂OCFH₂; —CF₂OCF₂H; —CF₂OCF₃; —CF₂OCF₂CF₃; —CF₂OCF₂CHF₂; —CF₂OCF₂CH₂F; —CF₂OCHFCF₃; —CF₂OCHFCHF₂; —CF₂OCHFCH₃; —CF₂OCHFCH₂F; —CF₂OCH₂CF₃; —CF₂OCH₂CHF₂; —CF₂OCH₂CH₂F;

—CH$_2$OCFH$_2$; —CH$_2$OCF$_2$H; —CH$_2$OCF$_3$; —CH$_2$OCF$_2$CF$_3$; —CH$_2$OCF$_2$CHF$_2$; —CH$_2$OCF$_2$CH$_3$; —CH$_2$OCF$_2$CH$_2$F; —CH$_2$OCHFCF$_3$; —CH$_2$OCHFCHF$_2$; —CH$_2$OCHFCH$_3$; —CH$_2$OCHFCH$_2$F; —CH$_2$OCH$_2$CF$_3$; —CH$_2$OCH$_2$CHF$_2$; —CH$_2$OCH$_2$CH$_2$F; —CHFOCFH$_2$; —CHFOCF$_2$H; —CHFOCF$_3$; —CHFOCF$_2$CF$_3$; —CHFOCF$_2$CHF$_2$; —CHFOCF$_2$CH$_3$; —CHFOCF$_2$CH$_2$F; —CHFOCHFCF$_3$; —CHFOCHFCHF$_2$; —CHFOCHFCH$_3$; —CHFOCHFCH$_2$F; —CHFOCH$_2$CF$_3$; —CHFOCH$_2$CHF$_2$; or —CHFOCH$_2$CH$_2$F.

Para. D. The electrolyte of Para. A, B, or C comprising a mixture of at least one compound of Formula I and at least one compound of Formula II.

Para. E. The electrolyte of any one of Paras. A-D further comprising a non-aqueous solvent.

Para. F. The electrolyte of Para. E, wherein the at least one compound of Formula I, Formula II, or mixture of any two or more thereof is present in the non-aqeuous solvent from about 0.01 wt % to about 50 wt %.

Para. G. The electrolyte of any one of Paras. E-F, wherein the non-aqueous solvent comprises a fluorinated carbonate, fluorinated ether, fluorinated ester, fluorinated amide, fluorinated carbamate compound, or a mixture of any two or more thereof.

Para. H. The electrolyte of any one of Paras. E-G the non-aqueous solvent comprises fluoroethylene carbonate, difluoroethylene carbonate, 4-(trifluoromethyl)-1,3-dioxolan-2-one, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, trifluoroethyl acetate, 2,2,2-trifluoro-N,N-dimethylacetamide, 2,2,2-trifluoroethyl dimethylcarbamate, or a mixture of any two or more thereof.

Para. I. The electrolyte of any one of Para. E, wherein the non-aqueous solvent comprises an ionic liquid.

Para. J. The electrolyte of Para. I, wherein the ionic liquid comprises a pyrrolidinium, piperidinium, imidazolium, ammonium, phosphonium, cyclic phosphonium, or sulfonium, with a counter ion of N(CF$_3$SO$_2$)$_2^-$, N(FSO$_2$)$_2^-$, N(CF$_3$CF$_2$SO$_2$)$_2^-$, C(CF$_3$SO$_2$)$_3^-$, CF$_3$SO$_3^-$, CF$_3$CO$_2^-$, N(CN)$_2^-$, or C$_2$F$_5$CO$_2^-$.

Para. K. The electrolyte of Para. E, wherein the non-aqueous solvent is a non-fluorinated, non-aqueous solvent.

Para. L. The electrolyte of Para. K, wherein the at least one compound of Formula I, Formula II, or mixture of any two or more thereof is present in the non-aqueous, non-fluorinated solvent from about 0.01 wt % to about 50 wt %.

Para. M. The electrolyte of any one of Paras. A-L further comprising a lithium salt.

Para. N. The electrolyte of Para. M, wherein the lithium salt comprises a lithium alkyl fluorophosphate; a lithium alkyl fluoroborates; lithium 4,5-dicyano-2-(trifluoromethyl) imidazole; lithium 4,5-dicyano-2-methylimidazole; trilithium 2,2',2''-tris(trifluoromethyl)benzotris(imidazolate); Li(CF$_3$CO$_2$); Li(C$_2$F$_5$CO$_2$); LiCF$_3$SO$_3$; LiCH$_3$SO$_3$; LiN(SO$_2$CF$_3$)$_2$; LiC(CF$_3$SO$_2$)$_3$; LiN(SO$_2$C$_2$F$_5$)$_2$; LiClO$_4$; LiBF$_4$; LiAsF$_6$; LiPF$_6$; LiPF$_2$(C$_2$O$_4$)$_2$; LiPF$_4$(C$_2$O$_4$); LiB(C$_2$O$_4$)$_2$; LiBF$_2$(C$_2$O$_4$)$_2$; Li$_2$(B$_{12}$X$_{12-n}$H$_n$); Li$_2$(B$_{10}$X$_{10-n'}$H$_{n'}$); or a mixture of any two or more thereof, wherein X is independently at each occurrence a halogen, n is an integer from 0 to 12, and n' is an integer from 0 to 10.

Para. O. The electrolyte of any one of Paras. A-L further comprising a sodium salt.

Para. P. The electrolyte of Para. O, wherein the sodium salt comprises Na(CF$_3$CO$_2$); Na(C$_2$F$_5$CO$_2$); NaClO$_4$; NaBF$_4$; NaAsF$_6$; NaPF$_6$; NaPF$_2$(C$_2$O$_4$)$_2$; NaPF$_4$(C$_2$O$_4$); NaCF$_3$SO$_3$; NaCH$_3$SO$_3$; NaN(SO$_2$CF$_3$)$_2$; NaC(CF$_3$SO$_2$)$_3$; NaN(SO$_2$C$_2$F$_5$)$_2$; sodium alkyl fluorophosphates; sodium alkyl fluoroborates; sodium 4,5-dicyano-2-(trifluoromethyl) imidazole; sodium 4,5-dicyano-2-methylimidazole; trisodium 2,2',2''-tris(trifluoromethyl)benzotris(imidazolate); NaB(C$_2$O$_4$)$_2$; NaBF$_2$(C$_2$O$_4$)$_2$; Na$_2$(B$_{12}$X$_{12-n}$H$_n$); Na$_2$(B$_{10}$X$_{10-n'}$H$_{n'}$); or a mixture of any two or more thereof, wherein X is independently at each occurrence a halogen, is an integer from 0 to 12 and n' is an integer from 0 to 10.

Para. Q. The electrolyte of any one of Paras. A-P further comprising an aprotic gel polymer carrier/solvent.

Para. R. The electrolyte of any one of Paras. A-Q further comprising an electrode stabilizing additive or redox shuttle molecules for overcharge protection.

Para. S. An electrochemical device comprising:
 a cathode;
 an anode; and
 an electrolyte;
 wherein the electrolyte comprises:
  a salt; and
  a fluorinated organosulfate compound represented by Formula I:

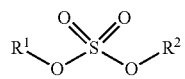

Formula I

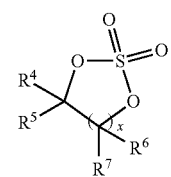

Formula II wherein:
 R$^1$ is alkyl, R$^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
 R$^2$ is alkyl, R$^3$O-alkyl-, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
 R$^3$ is H, alkyl, alkenyl, alkynyl, aryl, aralkyl, heteroaryl, heteroarylalkyl, heterocyclylalkyl, heterocyclylalkyl, cycloalkyl, cycloalkylalkyl, a polyalkylene glycol, silyl, or siloxy;
 x is 1 or 2;
 R$^4$ is H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR$^8$, —OC(O)R$^8$;
 R$^5$ is H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, a polyalkylene glycol, —C(O)OR$^8$, —OC(O)R$^8$;
 each R$^6$ is individually H, F, OR$^8$, alkyl, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, —C(O)OR$^8$, —OC(O)R$^8$;

each R$^7$ is individually H, F, OR$^8$, alkyl, alkenyl, alkynyl, aryl, aralkyl, heteroaryl, heteroarylalkyl, heterocyclylalkyl, heterocyclylalkyl, cycloalkyl, cycloalkylalkyl, silyl, siloxy, an ether, —C(O)OR$^8$, —OC(O)R$^8$;

or wherein R$^4$ and R$^5$ or R$^6$ and R$^7$ join together to form an =O group;

each R$^8$ is individually H, alkyl, alkenyl, aralkyl, polyalkylene glycol, or silyl; and at least one of R$^1$ and R$^2$ in Formula I is a fluorinated group, and/or at least one of R$^4$, R$^5$, R$^6$, or R$^7$ in Formula II is fluorine or is a fluorinated group.

Para. T. The electrochemical device of Para. S, wherein at least one of R$^1$ and R$^2$ is —CFH$_2$; —CF$_2$H; —CF$_3$; —CF$_2$CF$_3$; —CF$_2$CHF$_2$; —CF$_2$CH$_3$; —CF$_2$CH$_2$F; —CHFCF$_3$; —CHFCHF$_2$; —CHFCH$_3$; —CHFCH$_2$F; —CH$_2$CF$_3$; —CH$_2$CHF$_2$; —CH$_2$CH$_2$F; —CF(CF$_3$)$_2$; —CH(CF$_3$)$_2$; —CF$_2$CF$_2$CF$_3$; —CF$_2$CF$_2$CHF$_2$; —CF$_2$CF$_2$CH$_3$; —CF$_2$CF$_2$CH$_2$F; —CH$_2$CF$_2$CF$_3$; —CH$_2$CF$_2$CHF$_2$; —CH$_2$CF$_2$CH$_3$; —CH$_2$CF$_2$CH$_2$F; —CHFCF$_2$CF$_3$; —CHFCF$_2$CHF$_2$; —CHFCF$_2$CH$_3$; —CHFCF$_2$CH$_2$F; —CF$_2$CH$_2$CF$_3$; —CF$_2$CH$_2$CHF$_2$; —CF$_2$CH$_2$CH$_3$; —CF$_2$CH$_2$CH$_2$F; —CF$_2$CHFCF$_3$; —CF$_2$CHFCHF$_2$; —CF$_2$CHFCH$_3$; —CF$_2$CHFCH$_2$F; —CHFCHFCF$_3$; —CHFCHFCHF$_2$; —CHFCHFCH$_3$; —CHFCHFCH$_2$F; CH$_2$CH$_2$CF$_3$; —CH$_2$CH$_2$CHF$_2$; —CH$_2$CH$_2$CH$_2$F; —CF$_2$CF$_2$CF$_2$CF$_3$; —CF$_2$CF$_2$CF$_2$CH$_3$; —CF$_2$CF$_2$CF$_2$CHF$_2$; —CF$_2$CF$_2$CF$_2$CH$_2$F; —CH$_2$CF$_2$CF$_2$CF$_3$; —CH$_2$CF$_2$CF$_2$CH$_3$; —CH$_2$CF$_2$CF$_2$CHF$_2$; —CH$_2$CF$_2$CF$_2$CH$_2$F; —CHFCF$_2$CF$_2$CF$_3$; —CHFCF$_2$CF$_2$CH$_3$; —CHFCF$_2$CF$_2$CHF$_2$; —CHFCF$_2$CF$_2$CH$_2$F; —CF$_2$CH$_2$CF$_2$CF$_3$; —CF$_2$CH$_2$CF$_2$CH$_3$; —CF$_2$CH$_2$CF$_2$CHF$_2$; —CF$_2$CH$_2$CF$_2$CH$_2$F; —CF$_2$CHFCF$_2$CF$_3$; —CF$_2$CHFCF$_2$CH$_3$; —CF$_2$CHFCF$_2$CHF$_2$; —CF$_2$CHFCF$_2$CH$_2$F; —CHFCHFCF$_2$CF$_3$; —CHFCHFCF$_2$CH$_3$; —CHFCHFCF$_2$CHF$_2$; —CHFCHFCF$_2$CH$_2$F; —CH$_2$CH$_2$CF$_2$CF$_3$; —CH$_2$CH$_2$CF$_2$CH$_3$; —CH$_2$CH$_2$CF$_2$CHF$_2$; —CH$_2$CH$_2$CF$_2$CH$_2$F; —CF$_2$CF$_2$CF$_2$CF$_3$; —CF$_2$CF$_2$CF$_2$CF$_3$; —CF$_2$CF$_2$CF$_2$ CF$_2$CHF$_2$; —CH$_2$CF$_2$CF$_2$ CF$_2$CHF$_2$; —CF$_2$OCFH$_2$; —CF$_2$OCF$_2$H; —CF$_2$OCF$_3$; —CF$_2$OCF$_2$CF$_3$; —CF$_2$OCF$_2$CHF$_2$; —CF$_2$OCF$_2$CH$_3$; —CF$_2$OCF$_2$CH$_2$F; —CF$_2$OCHFCF$_3$; —CF$_2$OCHFCHF$_2$; —CF$_2$OCHFCH$_3$; —CF$_2$OCHFCH$_2$F; —CF$_2$OCH$_2$CF$_3$; —CF$_2$OCH$_2$CHF$_2$; —CF$_2$OCH$_2$CH$_2$F; —CH$_2$OCFH$_2$; —CH$_2$OCF$_2$H; —CH$_2$OCF$_3$; —CH$_2$OCF$_2$CF$_3$; —CH$_2$OCF$_2$CHF$_2$; —CH$_2$OCF$_2$CH$_3$; —CH$_2$OCF$_2$CH$_2$F; —CH$_2$OCHFCF$_3$; —CH$_2$OCHFCHF$_2$; —CH$_2$OCHFCH$_3$; —CH$_2$OCHFCH$_2$F; —CH$_2$OCH$_2$CF$_3$; —CH$_2$OCH$_2$CHF$_2$; —CH$_2$OCH$_2$CH$_2$F; —CHFOCFH$_2$; —CHFOCF$_2$H; —CHFOCF$_3$; —CHFOCF$_2$CF$_3$; —CHFOCF$_2$CHF$_2$; —CHFOCF$_2$CH$_3$; —CHFOCF$_2$CH$_2$F; —CHFOCHFCF$_3$; —CHFOCHFCHF$_2$; —CHFOCHFCH$_3$; —CHFOCHFCH$_2$F; —CHFOCH$_2$CF$_3$; —CHFOCH$_2$CHF$_2$; or —CHFOCH$_2$CH$_2$F.

Para. U. The electrochemical device of any one of Paras. S-T, wherein at least one R$^4$, R$^5$, R$^6$, or R$^7$ is F; —CFH$_2$; —CF$_2$H; —CF$_3$; —CF$_2$CF$_3$; —CF$_2$CHF$_2$; —CF$_2$CH$_3$; —CF$_2$CH$_2$F; —CHFCF$_3$; —CHFCHF$_2$; —CHFCH$_3$; —CHFCH$_2$F; —CH$_2$CF$_3$; —CH$_2$CHF$_2$; —CH$_2$CH$_2$F; —CF(CF$_3$)$_2$; —CH(CF$_3$)$_2$; —CF$_2$CF$_2$CF$_3$; —CF$_2$CF$_2$CHF$_2$; —CF$_2$CF$_2$CH$_3$; —CF$_2$CF$_2$CH$_2$F; —CH$_2$CF$_2$CF$_3$; —CH$_2$CF$_2$CHF$_2$; —CH$_2$CF$_2$CH$_3$; —CHFCF$_2$CF$_3$; —CHFCF$_2$CHF$_2$; —CHFCF$_2$CH$_3$; —CHFCF$_2$CH$_2$F; —CF$_2$CH$_2$CF$_3$; —CF$_2$CH$_2$CHF$_2$; —CF$_2$CH$_2$CH$_3$; —CF$_2$CH$_2$CH$_2$F; —CF$_2$CF$_2$CF$_2$CF$_3$; —CF$_2$CF$_2$CF$_2$CHF$_2$; —CF$_2$CF$_2$CF$_2$CH$_3$; —CF$_2$CF$_2$CF$_2$CH$_2$F; —CH$_2$CF$_2$CF$_2$CF$_3$; —CH$_2$CF$_2$CF$_2$CHF$_2$; —CH$_2$CF$_2$CF$_2$CH$_3$; —CH$_2$CF$_2$CF$_2$CH$_2$F; —CHFCF$_2$CF$_2$CF$_3$; —CHFCF$_2$CF$_2$CHF$_2$; —CHFCF$_2$CF$_2$CH$_2$F; —CF$_2$CH$_2$CF$_2$CF$_3$; —CF$_2$CH$_2$CF$_2$CH$_3$; —CF$_2$CH$_2$CF$_2$CHF$_2$; —CF$_2$CH$_2$CF$_2$CH$_2$F; —CF$_2$CHFCF$_2$CF$_3$; —CF$_2$CHFCF$_2$CHF$_2$; —CF$_2$CHFCF$_2$CH$_3$; —CF$_2$CHFCF$_2$CH$_2$F; —CHFCHFCF$_2$CF$_3$; —CHFCHFCF$_2$CHF$_2$; —CHFCHFCF$_2$CH$_2$F; —CH$_2$CH$_2$CF$_2$CF$_3$; —CH$_2$CH$_2$CF$_2$CH$_3$; —CH$_2$CH$_2$CF$_2$CHF$_2$; —CH$_2$CH$_2$CF$_2$CH$_2$F; —CF$_2$CF$_2$CF$_2$CF$_3$; —CH$_2$CF$_2$CF$_2$CF$_2$CF$_3$; —CF$_2$CF$_2$CF$_2$ CF$_2$CHF$_2$; —CH$_2$CF$_2$CF$_2$CF$_2$CHF$_2$; —CFH$_2$; —OCF$_2$H; —OCF$_3$; —OCF$_2$CF$_3$; —OCF$_2$CHF$_2$; —OCF$_2$CH$_3$; —OCF$_2$CH$_2$F; —OCHFCF$_3$; —OCHFCHF$_2$; —OCHFCH$_3$; —OCHFCH$_2$F; —OCH$_2$CF$_3$; —OCH$_2$CHF$_2$; —OCH$_2$CH$_2$F; CF$_2$OCFH$_2$; —CF$_2$OCF$_2$H; —CF$_2$OCF$_3$; —CF$_2$OCF$_2$CF$_3$; —CF$_2$OCF$_2$CHF$_2$; —CF$_2$OCF$_2$CH$_3$; —CF$_2$OCF$_2$CH$_2$F; —CF$_2$OCHFCF$_3$; —CF$_2$OCHFCHF$_2$; —CF$_2$OCHFCH$_3$; —CF$_2$OCHFCH$_2$F; —CF$_2$OCH$_2$CF$_3$; —CF$_2$OCH$_2$CHF$_2$; —CF$_2$OCH$_2$CH$_2$F; —CH$_2$OCFH$_2$; —CH$_2$OCF$_2$H; —CH$_2$OCF$_3$; —CH$_2$OCF$_2$CF$_3$; —CH$_2$OCF$_2$CHF$_2$; —CH$_2$OCF$_2$CH$_3$; —CH$_2$OCF$_2$CH$_2$F; —CH$_2$OCHFCF$_3$; —CH$_2$OCHFCHF$_2$; —CH$_2$OCHFCH$_3$; —CH$_2$OCHFCH$_2$F; —CH$_2$OCH$_2$CF$_3$; —CH$_2$OCH$_2$CHF$_2$; —CH$_2$OCH$_2$CH$_2$F; —CHFOCFH$_2$; —CHFOCF$_2$H; —CHFOCF$_3$; —CHFOCF$_2$CF$_3$; —CHFOCF$_2$CHF$_2$; —CHFOCF$_2$CH$_3$; —CHFOCF$_2$CH$_2$F; —CHFOCHFCF$_3$; —CHFOCHFCHF$_2$; —CHFOCHFCH$_3$; —CHFOCHFCH$_2$F; —CHFOCH$_2$CF$_3$; —CHFOCH$_2$CHF$_2$; or —CHFOCH$_2$CH$_2$F.

Para. V. The electrochemical device of any one of Paras. S-U comprising a mixture of at least one compound of Formula I and at least one compound of Formula II.

Para. W. The electrochemical device of any one of Paras. S-V, the electrolyte further comprises a non-fluorinated solvent.

Para. X. The electrochemical device of any one of Paras. S-W further comprising a non-aqueous solvent.

Para. Y. The electrochemical device of Para. X, wherein the at least one compound of Formula I, Formula II, or mixture of any two or more thereof is present in the non-aqueous solvent from about 0.01 wt % to about 50 wt %.

Para. Z. The electrochemical device of any one of Paras. S-Y, wherein the electrolyte further comprises a lithium salt.

Para. A'. The electrochemical device of Para. Z, wherein the lithium salt comprises a lithium alkyl fluorophosphate; a lithium alkyl fluoroborates; lithium 4,5-dicyano-2-(trifluoromethyl)imidazole; lithium 4,5-dicyano-2-methylimidazole; trilithium 2,2',2"-tris(trifluoromethyl)benzotris(imidazolate); Li(CF$_3$CO$_2$); Li(C$_2$F$_5$CO$_2$); LiCF$_3$SO$_3$; LiCH$_3$SO$_3$; LiN(SO$_2$CF$_3$)$_2$; LiC(CF$_3$SO$_2$)$_3$; LiN(SO$_2$C$_2$F$_5$)$_2$; LiClO$_4$; LiBF$_4$; LiAsF$_6$; LiPF$_6$; LiPF$_2$(C$_2$O$_4$)$_2$; LiPF$_4$(C$_2$O$_4$); LiB(C$_2$O$_4$)$_2$; LiBF$_2$(C$_2$O$_4$)$_2$; Li$_2$(B$_{12}$X$_{12-n}$H$_n$); Li$_2$(B$_{10}$X$_{10-n}$H$_n$); or a mixture of any two or more thereof, wherein X is independently at each occurrence a halogen, n is an integer from 0 to 12, and n' is an integer from 0 to 10.

Para. B'. The electrochemical device of any one of Paras. S-Y, wherein the electrolyte further comprises a sodium salt.

Para. C'. The electrochemical device of Para. B', wherein the sodium salt comprises $Na(CF_3CO_2)$; $Na(C_2F_5CO_2)$; $NaClO_4$; $NaBF_4$; $NaAsF_6$; $NaPF_6$; $NaPF_2(C_2O_4)_2$; $NaPF_4(C_2O_4)$; $NaCF_3SO_3$; $NaCH_3SO_3$; $NaN(SO_2CF_3)_2$; $NaC(CF_3SO_2)_3$; $NaN(SO_2C_2F_5)_2$; sodium alkyl fluorophosphates; sodium alkyl fluoroborates; sodium 4,5-dicyano-2-(trifluoromethyl)imidazole; sodium 4,5-dicyano-2-methylimidazole; trisodium 2,2',2''-tris(trifluoromethyl)benzotris(imidazolate); $NaB(C_2O_4)_2$; $NaBF_2(C_2O_4)_2$; $Na_2(B_{12}X_{12-n}H_n)$; $Na_2(B_{10}X_{10-n}H_{n'})$; or a mixture of any two or more thereof, wherein X is independently at each occurrence a halogen, is an integer from 0 to 12 and n' is an integer from 0 to 10.

Para. D'. The electrochemical device of any one of Paras. S-C', wherein the electrolyte further comprises an aprotic gel polymer carrier/solvent.

Para. E'. The electrochemical device of any one of Paras. S-D', wherein the electrolyte further comprises electrode stabilizing additive or redox shuttle molecules for overcharge protection.

Para. F'. The electrochemical device of any one of Paras. S-E' further comprising a separator between the anode and cathode.

Para. G'. The electrochemical device of any one of Paras. S-F' which is a lithium-ion secondary battery, a lithium-sulfur secondary battery, a lithium-air secondary battery, a sodium-ion secondary battery, a sodium-sulfur secondary battery, or a sodium-air secondary battery.

Para. H'. The electrochemical device of any one of Paras. S-G', wherein the cathode comprises a spinel, an olivine, a surface modified olivine $LiFePO_4$, $LiMn_{0.5}Ni_{0.5}O_2$, $LiCoO_2$, $LiNiO_2$, $LiNi_{1-x}Co_yMe_zO_2$, $LiNi_\alpha Mn_\beta Co_\gamma O_2$, $LiMn_2O_4$, $LiFeO_2$, $LiNi_{0.5}Me_{1.5}O_4$, $Li_{1+x}Ni_h Mn_k Co_j Me^2_y O_{2-z} F_z$, $VO_2$ or $E_{x''}F_2(Me_3O_4)_3$, $LiNi_m Mn_n O_4$, wherein Me is Al, Mg, Ti, B, Ga, Si, Mn, or Co; $Me^2$ is Mg, Zn, Al, Ga, B, Zr, or Ti; E is Li, Ag, Cu, Na, Mn, Fe, Co, Ni, or Zn; F is Ti, V, Cr, Fe, or Zr; wherein $0 \le x \le 0.3$; $0 \le y \le 0.5$; $0 \le z \le 0.5$; $0 \le m \le 2$; $0 \le n \le 2$; $0 \le x' \le 0.4$; $0 \le \alpha \le 1$; $0 \le \beta \le 1$; $0 \le \gamma \le 1$; $0 \le h \le 1$; $0 \le k \le 1$; $0 \le l \le 1$; $0 \le y' \le 0.4$; $0 \le z' \le 0.4$; and $0 \le x'' \le 3$; with the proviso that at least one of h, k and l is greater than 0.

Para. I'. The electrochemical device of any one of Paras. S-G', wherein the cathode comprises a layered structure, a spinel, a olivine with and without coating material including, but not limited to carbon, polymer, fluorine, metal oxides, $NaFePO_4$, $NaCoO_2$, $NaNiO_2$, $NaMn_2O_4$, or $Na_{1-x}Ni_\alpha Co_\beta Mn_\gamma M_\delta O_{2-z}N_z$, wherein M is Li, Al, Mg, Ti, B, Ga, Si, Zr, Zn, Cu, Fe; N is F, Cl, S; wherein $0 \le x \le 1$, $0 \le \alpha \le 1$, $0\beta > 1$, $0 \le \gamma \le 1$, $0 \le \delta \le 1$, $0 \le z \le 2$; with the proviso that at least one of $\alpha$, $\beta$ and $\gamma$ is greater than 0.

Para. J'. The electrochemical device of any one of Paras. S-I', wherein the anode comprises natural graphite, synthetic graphite, hard carbon, amorphous carbon, soft carbon, mesocarbon microbeads (MCMB), acetylene black, Ketjen black, carbon black, mesoporous carbon, porous carbon matrix, carbon nanotube, carbon nanofiber, graphene, silicon microparticle, silicon nanoparticle, silicon-carbon composite, tin microparticle, tin nanoparticle, tin-carbon composite, silicon-tin composite, phosphorous-carbon composites, black phosphorus, red phosphorus, mixture of red and black phosphorus, lithium titanium oxide, lithium metal, sodium metal, lithium titanium oxide or magnesium metal.

Para. K'. The electrochemical device of Para. S-J', wherein, wherein the anode comprises synthetic graphite, natural graphite, amorphous carbon, hard carbon, soft carbon, acetylene black, MCMB, carbon black, Ketjen black, mesoporous carbon, porous carbon matrix, carbon nanotube, carbon nanofiber, graphene, black phosphorus, red phosphorus, mixture of red and black phosphorus, Ge, SnSb, $NiCo_2O_4$, $Sb_2O_4$, or $Co_3O_4$.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrolyte comprising:
   a salt;
   a solvent comprising 2,2,2-(trifluoroethyl)methyl carbonate; and
   an additive comprising 4-(trifluoromethyl)-1,3,2-dioxathiolane 2,2-dioxide.

2. The electrolyte of claim 1, wherein the 4-(trifluoromethyl)-1,3,2-dioxathiolane 2,2-dioxide is present in the non-aqueous solvent from about 0.01 wt % to about 50 wt %.

3. The electrolyte of claim 1, wherein the salt is a lithium salt.

4. The electrolyte of claim 3, wherein the lithium salt comprises a lithium alkyl fluorophosphate; a lithium alkyl fluoroborates; lithium 4,5-dicyano-2-(trifluoromethyl)imidazole; lithium 4,5-dicyano-2-methylimidazole; trilithium 2,2',2''-tris(trifluoromethyl)benzotris(imidazolate); $Li(CF_3CO_2)$; $Li(C_2F_5CO_2)$; $LiCF_3SO_3$; $LiCH_3SO_3$; $LiN(SO_2CF_3)_2$; $LiC(CF_3SO_2)_3$; $LiN(SO_2C_2F_5)_2$; $LiClO_4$; $LiBF_4$; $LiAsF_6$; $LiPF_6$; $LiPF_2(C_2O_4)_2$; $LiPF_4(C_2O_4)$; $LiB(C_2O_4)_2$; $LiBF_2(C_2O_4)_2$; $Li_2(B_{12}X_{12-n}H_n)$; $Li_2(B_{10}X_{10-n'}H_{n'})$; or a mixture of any two or more thereof, wherein X is independently at each occurrence a halogen, n is an integer from 0 to 12, and n' is an integer from 0 to 10.

5. An electrochemical device comprising:
   a cathode;
   an anode; and
   the electrolyte of claim 1.

6. The electrochemical device of claim 5 wherein the 4-(trifluoromethyl)-1,3,2-dioxathiolane 2,2-dioxide is present in the electrolyte from about 0.01 wt % to about 50 wt %.

7. The electrochemical device of claim 5, wherein a volume ratio of the 2,2,2-trifluoroethyl)methyl carbonate to the 4-(trifluoromethyl)-1,3,2-dioxathiolane 2,2-dioxide is 7:3.

8. The electrochemical device of claim 5, wherein the salt is lithium hexafluorophosphate or sodium hexafluorophosphate.

9. The electrochemical device of claim 5, wherein the electrolyte consists of:
   a salt that is lithium or sodium hexafluorophosphate;
   2,2,2-(trifluoroethyl)methyl carbonate; and
   4-(trifluoromethyl)-1,3,2-dioxathiolane 2,2-dioxide.

10. The electrochemical device of claim 5, wherein the anode comprises synthetic graphite, natural graphite, amorphous carbon, hard carbon, soft carbon, acetylene black, MCMB, carbon black, Ketjen black, mesoporous carbon, porous carbon matrix, carbon nanotube, carbon nanofiber, graphene, black phosphorus, red phosphorus, mixture of red and black phosphorus, Ge, SnSb, $NiCo_2O_4$, $Sb_2O_4$, or $Co_3O_4$.

11. The electrochemical device of claim 5 is a lithium-ion secondary battery, a lithium-sulfur secondary battery, a lithium-air secondary battery, a sodium-ion secondary battery, a sodium-sulfur secondary battery, or a sodium-air secondary battery.

* * * * *